(12) United States Patent
Chalker, Sr. et al.

(10) Patent No.: US 10,590,012 B2
(45) Date of Patent: Mar. 17, 2020

(54) SULFUR-LIMONENE POLYSULFIDE

(71) Applicants: THE UNIVERSITY OF TULSA, Tulsa, OK (US); FLINDERS UNIVERSITY OF SOUTH AUSTRALIA, Bedford Park (AU)

(72) Inventors: Justin M. Chalker, Sr., Clarence Park (AU); Michael P. Crockett, Brighton, MA (US); Austin M. Evans, Broken Arrow, OK (US); Max Worthington, Glenalta (AU)

(73) Assignee: The University of Tulsa, Tulsa, OK (US)

( * ) Notice: Subject to any disclaimer, the term of this patent is extended or adjusted under 35 U.S.C. 154(b) by 369 days.

(21) Appl. No.: 15/521,099

(22) PCT Filed: Oct. 13, 2015

(86) PCT No.: PCT/US2015/055205
§ 371 (c)(1),
(2) Date: Oct. 26, 2017

(87) PCT Pub. No.: WO2016/064615
PCT Pub. Date: Apr. 28, 2016

(65) Prior Publication Data
US 2018/0148346 A1    May 31, 2018

Related U.S. Application Data

(60) Provisional application No. 62/068,074, filed on Oct. 24, 2014.

(51) Int. Cl.
*B01J 20/22* (2006.01)
*C02F 1/28* (2006.01)
(Continued)

(52) U.S. Cl.
CPC .............. *C02F 1/285* (2013.01); *B01J 20/22* (2013.01); *B01J 20/262* (2013.01);
(Continued)

(58) Field of Classification Search
CPC ....................................................... C02F 1/285
(Continued)

(56) References Cited

U.S. PATENT DOCUMENTS 2,537,297 A    4/1948  Alexander
2,445,983 A    7/1948  Watson
(Continued)

FOREIGN PATENT DOCUMENTS

EP    0201197 A1    11/1986
WO    9521704 A1    8/1995

OTHER PUBLICATIONS

International Search Report and Written Opinion of the International Searching Authority dated Jan. 7, 2016, filed in related application PCT/US15/055205.
(Continued)

*Primary Examiner* — Duc Truong
(74) *Attorney, Agent, or Firm* — McAfee & Taft

(57) ABSTRACT

Disclosed is a limonene-sulfur polysulfide and methods for preparing the same. The polysulfide prepared according to these methods is flexible, moldable and otherwise capable of being formed in any manner consistent with a thermoplastic polymer. The limonene-sulfur polysulfide has been demonstrated to sequester inorganic palladium and inorganic mercury dissolved in water.

35 Claims, 38 Drawing Sheets

(51) Int. Cl.
| | |
|---|---|
| *C07C 319/22* | (2006.01) |
| *B01J 20/30* | (2006.01) |
| *B01J 20/26* | (2006.01) |
| *B01J 20/32* | (2006.01) |
| *C07C 321/22* | (2006.01) |
| *C02F 101/20* | (2006.01) |
| *C02F 103/00* | (2006.01) |
| *C02F 101/10* | (2006.01) |

(52) U.S. Cl.
CPC ....... *B01J 20/3078* (2013.01); *B01J 20/3085* (2013.01); *B01J 20/3253* (2013.01); *C07C 319/22* (2013.01); *C07C 321/22* (2013.01); *C02F 2101/10* (2013.01); *C02F 2101/20* (2013.01); *C02F 2103/007* (2013.01)

(58) Field of Classification Search
USPC ........................................................ 528/389
See application file for complete search history.

(56) References Cited

U.S. PATENT DOCUMENTS

| | | |
|---|---|---|
| 6,399,849 B1 | 6/2002 | Kalb et al. |
| 2012/0322918 A1 | 12/2012 | Lopez Gomez et al. |

OTHER PUBLICATIONS

Method 245.1 Determination of Mercury in Water by Cold Vapor Atomic Absorption Spectrometry, Revision 3.0, EMMC Version, J.W. O'Dell, B.B. Potter, L.B. Lobring and T.D. Martin dated 1994.
An Overview of Mercury and Methods for its Analysis, Microbac Laboratories, Inc. dated 2005.
Immobilization of Hg(II) in Water With Polysulfide-Rubber (PSR) Polymer-Coated Activated Carbon, Water Research, vol. 45, Issue 2, Jan. 2011, Eun-Ah Kim, Angelia Seyfferth, Scott Fendorf, Richard G. Luthy.
Limonene, Natural Product Reports, S.A. Firmenich dated 1989.
Methods for Sampling/Analysis of Mercury in Water and Solids.
Mercury Speciation in the Presence of Polysulfides, Environ. Sci. Technol. 2000, vol. 34, Jenny Jay, Francios Morel and Harold Hemond.
Lopez Gomez et al. Method for Stabilizing Liquid Mercury Using Sulfur Polymer Cement, via Mercury Sulfide. Patent No. US 2012/0322918 A1. Dec. 20, 2012.
Wetikamp, A. W., I. The Action of Sulfur on Terpenes. The Limonene Sulfides. J. Am. Chem. Soc. 1959, 81, 3430-3434.
Illa, O.; Namutebi, M.; Saha, C.; Ostovar, M.; Chen, C. C.; Haddow, M. F.; Nocquet-Thibault, S.; Lusi, M.; McGarrigle, E. M.; Aggarwal, V. K., Practical and Highly Selective Sulfur Ylide-Mediated Asymmetric Epoxidations and Aziridinations Using a Cheap and Readily Available Chiral Sulfide: Extensive Studies to Map Out Scope, Limitations, and Rationalization of Diastereo- and Enantioselectivities. J. Am. Chem. Soc. 2013, 135, 11951-11966.
Currell, B. R.; Williams, A. J,; Mooney, A. J.; Nash, B. J., Plasticization of Sulfur, West, J., Ed. American Chemical Society: Washington, DC, 1975; vol. 140, pp. 1-17.
Chung, W. J.; Griebel, J. J.; Kim, E. T.; Yoon, H.; Simmonds, A. G.; Ji, H. J.; Dirlam, P. T.; Glass, R. S.; Wie, J. J.; Nguyen, N. A.; Guralnick, B. W.; Park, J.; Somogyi, Á.; Theato, P.; Mackay, M. E.; Sung, Y.-E.; Char, K.; Pyun, J., The use of elemental sulfur as an alternative feedstock for polymeric materials. Nat. Chem. 2013, 5, 518-524.
Polymer electrodes: Simmonds, A. G.; Griebel, J. J.; Park, J.; Kim, K. R.; Chung, W. J.; Oleshko, V. P.; Kim, J.; Kim, E. T.; Glass, R. S.; Soles, C. L.; Sung, Y.-E.; Char, K.; Pyun, J., Inverse Vulcanization of Elemental Sulfur to Prepare Polymeric Electrode Materials for Li—S Batteries. ACS Macro Lett. 2014, 3, 229-232.
Infrared lenses: Griebel, J. J.; Namnabat, S.; Kim, E. T.; Himmelhuber, R.; Moronta, D. H.; Chung, W. J.; Simmonds, A. G.; Kim, K.-J.; Laan, J. v. d.; Nguyen, N. A.; Dereniak, E. L.; Mackay, M. E.; Char, K.; Glass, R. S.; Norwood, R. A.; Pyun, J., New Infrared Transmitting Material via Inverse Vulcanization of Elemental Sulfur to Prepare High Refractive Index Polymers. Adv. Mater. 2014, 26, 3014-3018.
Treatment Technologies for Mercury in Soil, Waste, and Water. U.S. Enviromental Protection Agency. 2007.
Aqueous Mercury Treatment. U.S. Environmental Protection Agency. 1997.
P.D. Kalb; J.W. Adams; L.W. Milian. Sulfur Polymer Stabilization/Solidification (SPSS) Treatment of Mixed-Waste Mercury Recovered from Environmental Restoration Activities at BNL. 2001.
Kalb et al. Treatment of Mercury Containing Waste. U.S. Pat. No. 6,399,849 B1. Jun. 4, 2002.

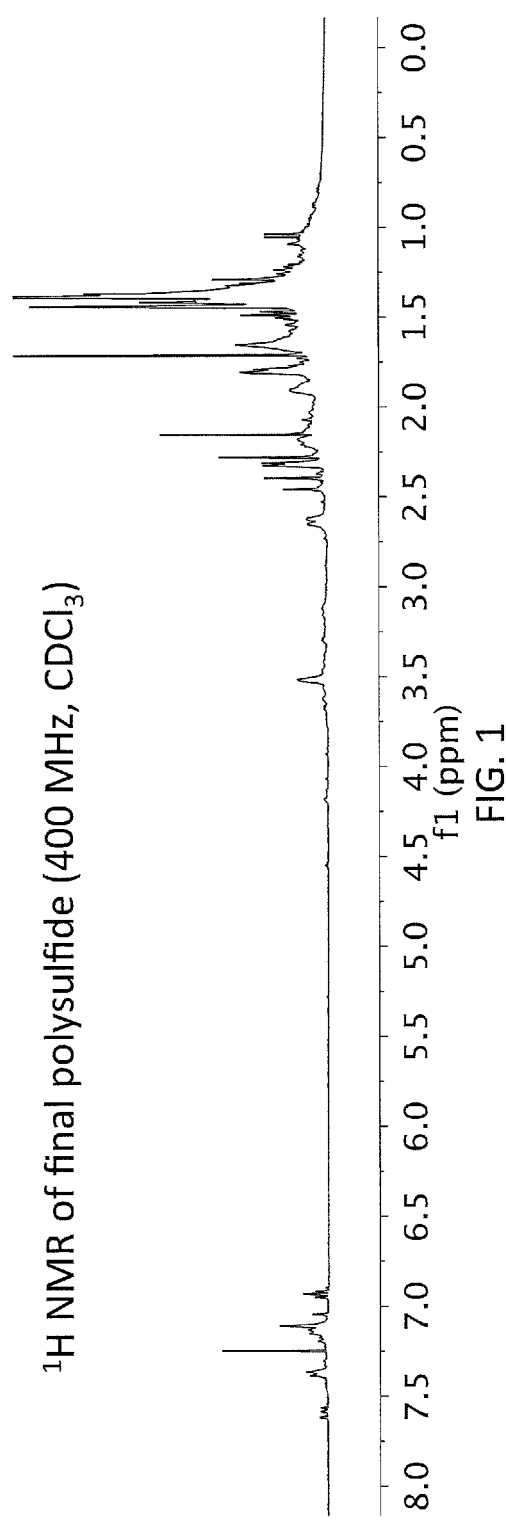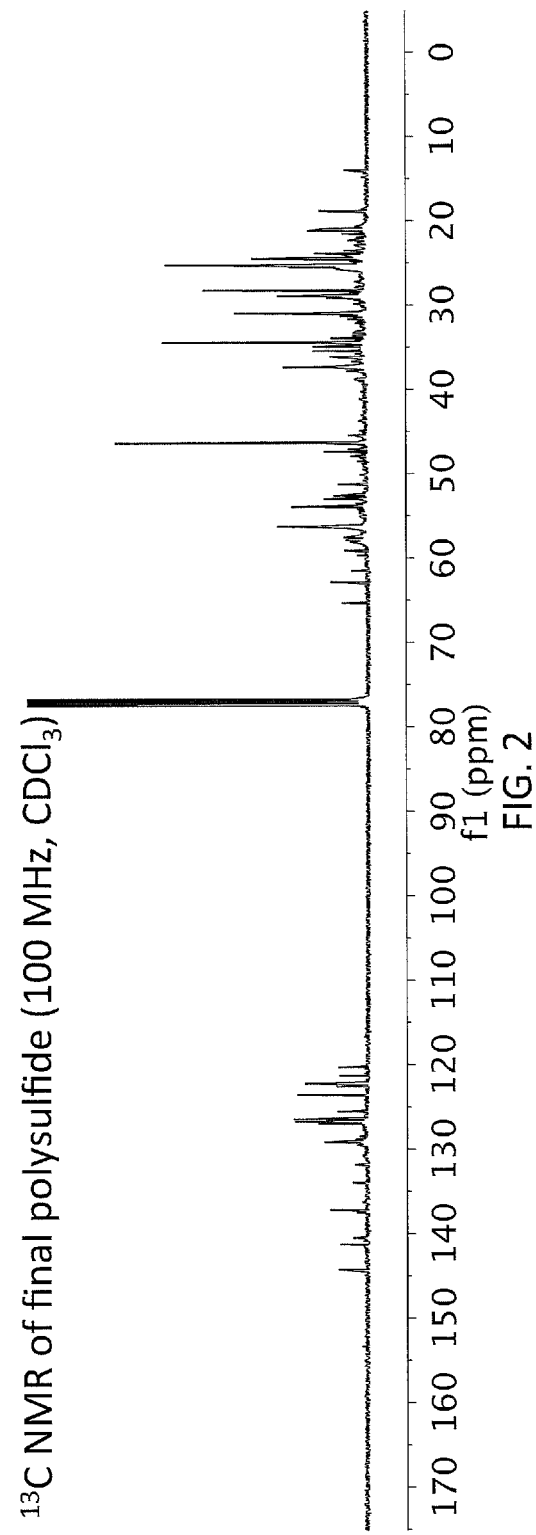

SULFUR-LIMONENE POLYSULFIDE

CROSS RELATED

This application claims the benefit of previously filed International Application PCT/US2015/055205 filed Oct. 13, 2015, and Provisional Application Ser. No. 62/068,074 filed on Oct. 24, 2014.

BACKGROUND

Palladium contamination, i.e. palladium (II), of the environment as a result of large scale organic synthesis processes and catalytic converter exhaust will continue to necessitate remediation of lakes, rivers and streams. Similarly, mercury contamination of the environment has resulted from decades of mining operations, metal refining processes, coal combustion and other industrial activities. Mercury, in the form of mercury (II) is extremely toxic and can cause kidney damage, embryotoxic effects and other health concerns. Efficient removal of such contaminants from the environment without exacerbating the problem by creating additional pollutant wastes will substantially improve our ecosystems.

SUMMARY

Disclosed herein is a novel sulfur-limonene polysulfide. The sulfur-limonene polysulfide has a generally transparent red colorization. Upon exposure to sufficient levels of mercury (II), the site of exposure on the sulfur-limonene polysulfide changes from red to yellow. The sulfur-limonene polysulfide is a reaction product of limonene, (R)-(+)-Limonene, (S)-(−)-Limonene and mixtures thereof, with elemental sulfur, i.e. $S_8$. The sulfur-limonene polysulfide has thermoplastic characteristics.

Additionally, the present disclosure provides methods for preparing the sulfur-limonene polysulfide. The method comprises heating sulfur to a temperature sufficient to melt the sulfur, adding limonene to the molten sulfur and allowing the two component mixture to react thereby forming a single phase comprising sulfur-limonene polysulfide. Typically, the reaction between the molten sulfur and limonene will occur at temperatures between about 130° C. and about 200° C. When necessary, as determined by the object formed from the sulfur-limonene polysulfide, the method includes further steps to remove undesirable volatile by-products. The resulting sulfur-limonene polysulfide has thermoplastic characteristics suitable for forming into an object using any conventional manufacturing or molding technique.

Further, the present disclosure describes methods for sequestering both palladium (II) and mercury (II) from aqueous solutions. The sequestering methods expose the aqueous solutions to the sulfur-limonene polysulfide at ambient conditions.

Finally, the present disclosure also describes methods for extracting palladium (II) and mercury (II) from soil by an aqueous extraction process and subsequently sequestering the palladium (II) and mercury (II) from the aqueous solution using the sulfur-limonene polysulfide.

BRIEF DESCRIPTION OF THE DRAWINGS

FIG. 1 is a $^1$H NMR for the polysulfide.
FIG. 2 is a $^{13}$C NMR for the polysulfide.

DETAILED DESCRIPTION

This disclosure provides a novel form of polysulfide and methods for preparing the disclosed polysulfide. Additionally, this disclosure describes methods for recovering mercury and palladium from water using the novel form of polysulfide. The novel form of polysulfide is a reaction product of limonene, either (R)-(+)-Limonene, also known as d-Limonene, or (S)-(−)-Limonene an enantiomeric form of d-Limonene and elemental sulfur. The resulting polysulfide is identified as a sulfur-limonene polysulfide and referred to herein as polysulfide. Either form of limonene will provide the necessary polysulfide. As such, when used herein the word limonene refers to both enantiomers.

The combined carbon and hydrogen content of the polymer may range from about 25% to about 50% by weight and the sulfur content may range from about 50% to about 75% by weight. Typically, the combined carbon and hydrogen content will range from about 40% to about 50% and the sulfur content may range from about 50% to about 60%. Preferably, the carbon+hydrogen to sulfur ratio will provide a polymer having a glass transition value sufficient to impart flexibility to products molded from the polymer.

Figure 40:
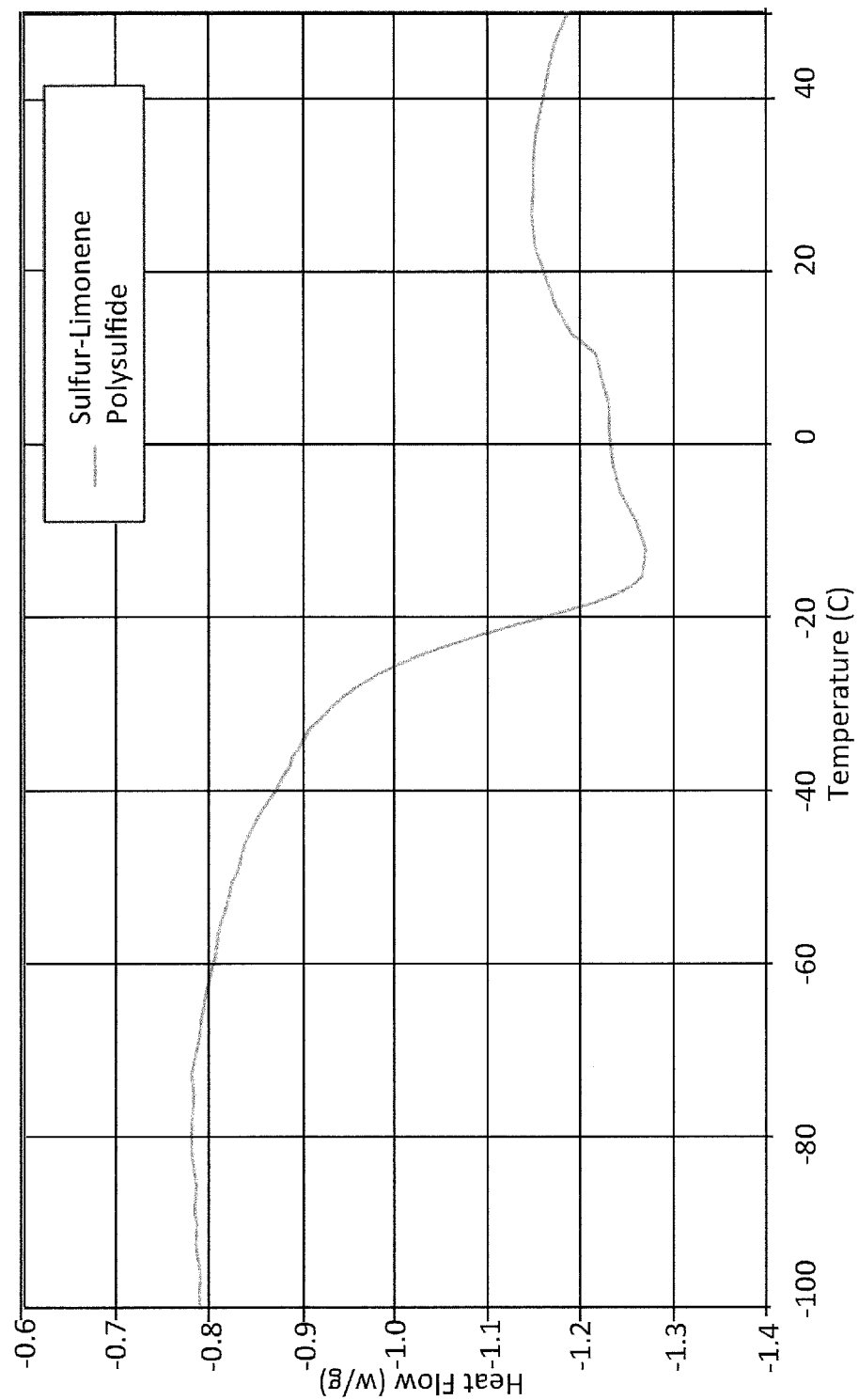
FIG. 40 depicts the results of differential scanning calorimetry analysis of the novel polysulfide.

The polysulfide having the above characteristics is not brittle and may be formed into a plurality of objects. See for example FIG. 9. Differential scanning calorimetry (DSC) revealed a glass transition ($T_g$) at −21° C. and simultaneous thermal analysis indicated substantial thermal decomposition about 200° C. The DSC scan of FIG. 40 shows a broad step change with a midpoint at −21° C. indicative of a low molecular weight polymer. The polysulfide prepared according to the method disclosed herein is preferably free of unreacted or crystalline sulfur. The final solid product has a red color yet is transparent in nature. The polysulfide is insoluble in water, sparingly soluble in methanol and fully soluble in dichloromethane, chloroform and tetrahydrofuran.

Figure 36:
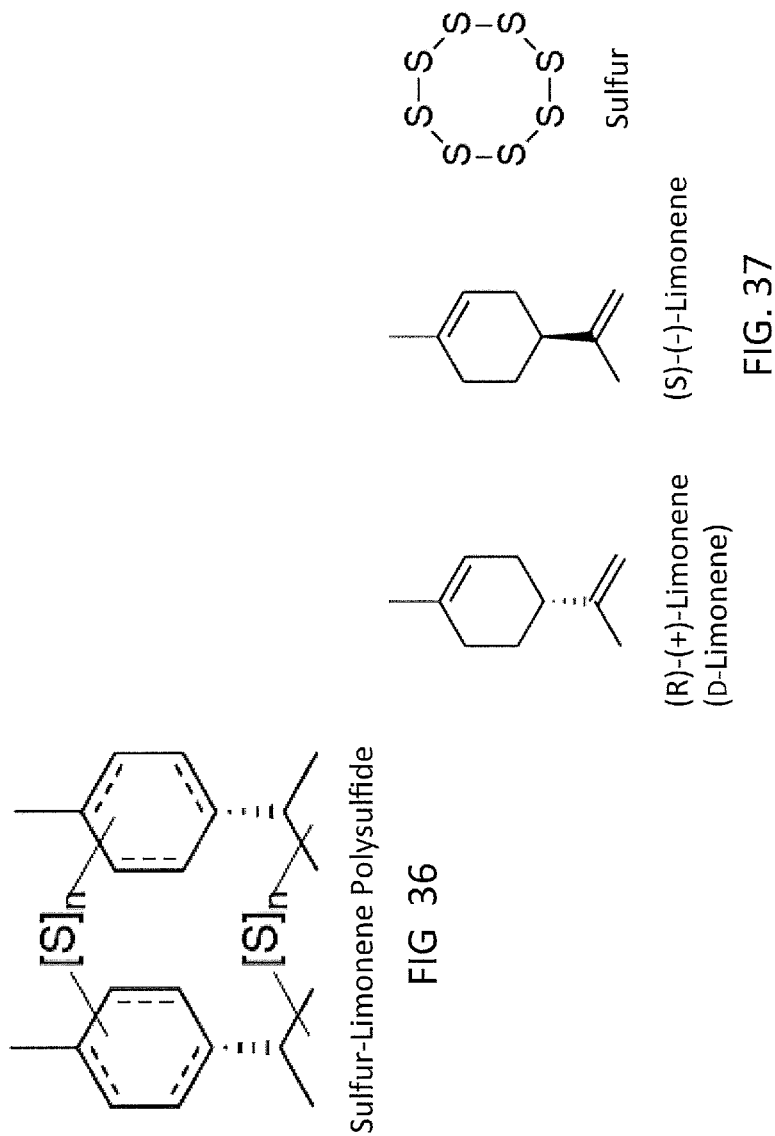
FIG. 36 depicts the predicted structure of the novel polysulfide.

When examined using analytical techniques, the polysulfide produced the scans provided in FIGS. 1-7. In view of the $^1H$, $^{13}C$, and HSQC NMR scans, the resulting polysulfide has an aromatic component. Based on mass analysis and elemental composition, the final polysulfide is believed to contain an average of 2 limonene units and 10 sulfur atoms as depicted in FIG. 36. However, the polysulfide can vary from one to three limonene units and may contain 2 to 19 sulfur atoms.

The NMR data reflects the following:
  0.75-2.55 ppm hydrogen associated with limonene domains that are greater than 2 bonds from sulfur atoms;
  2.5-4.5 ppm hydrogens positioned within 2 bonds of sulfur;
  6.75-8.0 ppm hydrogen associated with aromatic rings.

In FIG. 1, the $^1H$ NMR (400 MHz, CDCl$_3$) depicts the following peaks associated with the polysulfide: 7.62, 7.58, 7.56, 7.38, 7.36, 7.19, 7.15, 7.11, 7.04, 6.95, 6.93, 6.91, 3.52, 2.65, 2.62, 2.46, 2.40, 2.32, 2.31, 2.28, 2.15, 1.91, 1.81, 1.80, 1.71, 1.66, 1.50, 1.49, 1.44, 1.39, 1.29, 1.05, 1.04. In FIG. 2, the $^{13}C$ NMR (100 MHz, CDCl$_3$) depicts the following peaks associated with the polysulfide: 144.3, 141.2, 140.5, 137.2, 133.9, 131.9, 129.2, 127.0, 126.7, 126.4, 125.5, 123.6, 122.6, 122.2, 121.3, 120.29, 65.3, 62.8, 61.5, 59.7, 59.1, 58.1, 57.5, 56.3, 53.9, 52.99, 52.6, 51.2, 47.9, 47.4, 46.3, 37.4, 36.1, 35.4, 34.5, 31.0, 29.1, 28.9, 28.3, 25.3, 24.5, 23.9, 21.2, 20.9, 18.8.

To determine the UV-Vis spectrum for the polysulfide, two samples of the polysulfide were dissolved in CH$_2$Cl$_2$. The first sample had a concentration of 5.6 mg/mL and the second sample had a concentration of 1.86 mg/mL. UV-Vis analysis was carried out using a quartz cuvette. As reflected in FIG. 4, local absorbance maximum was observed at 420 nm. The determined absorbance is consistent with red colorization of the resulting polymer prior to sequestration of mercury (II). Additionally, with reference to FIG. 1, the alkene peaks associated with limonene are not present in the NMR scan of the polysulfide. The absence of the alkene peaks reflects the complete or at least substantially complete consumption of limonene in the polymerization reaction.

Without intending to be bound by theory, the reaction of limonene and sulfur is believed to follow a radical mechanism. First, sulfur cleaves homolytically to provide thiyl radicals. Next, the thiyl radicals add to the alkenes of limonene. The resulting radical on limonene propagates the reaction by reacting further with sulfur. Elimination reactions can lead to aromatization of a portion of the polysulfide.

Figure 3:
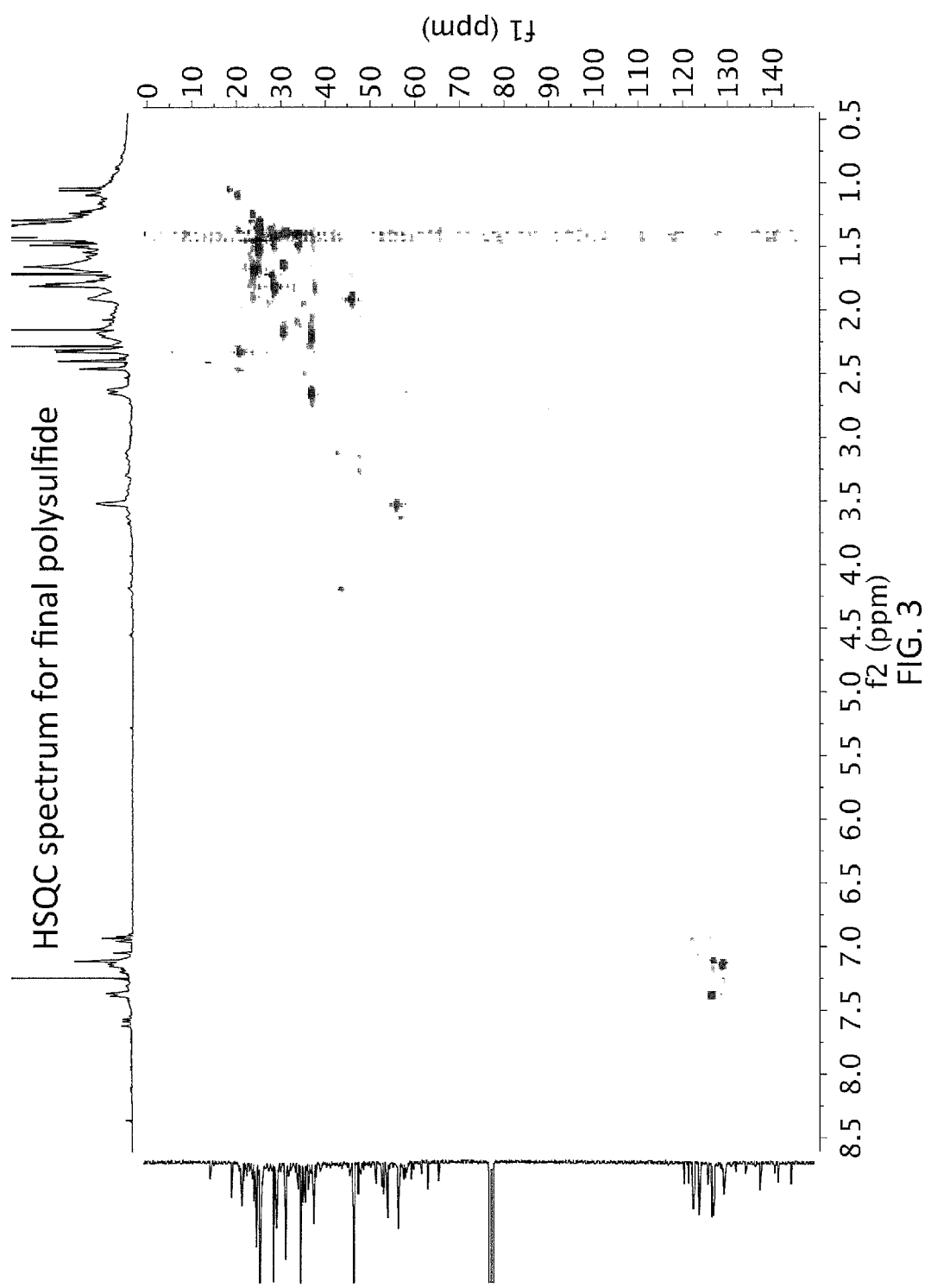
FIG. 3 provides Heteronuclear Single Quantum Coherence scan of the polysulfide.
Figure 4:
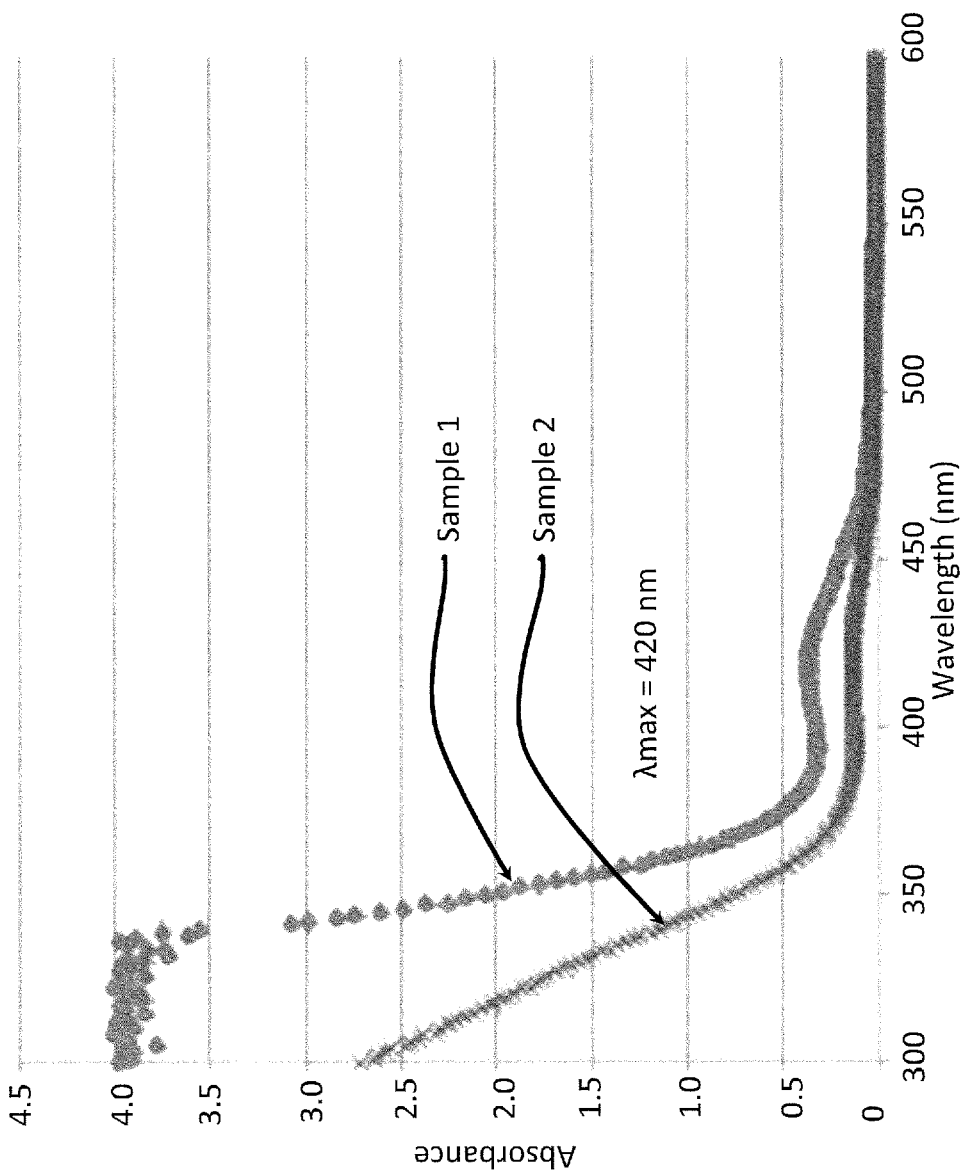
FIG. 4 is a UV-Vis spectrum for the polysulfide dissolved in $CH_2Cl_2$ at 5.6 mg/mL and at 1.86 mg/mL.
Figure 5:
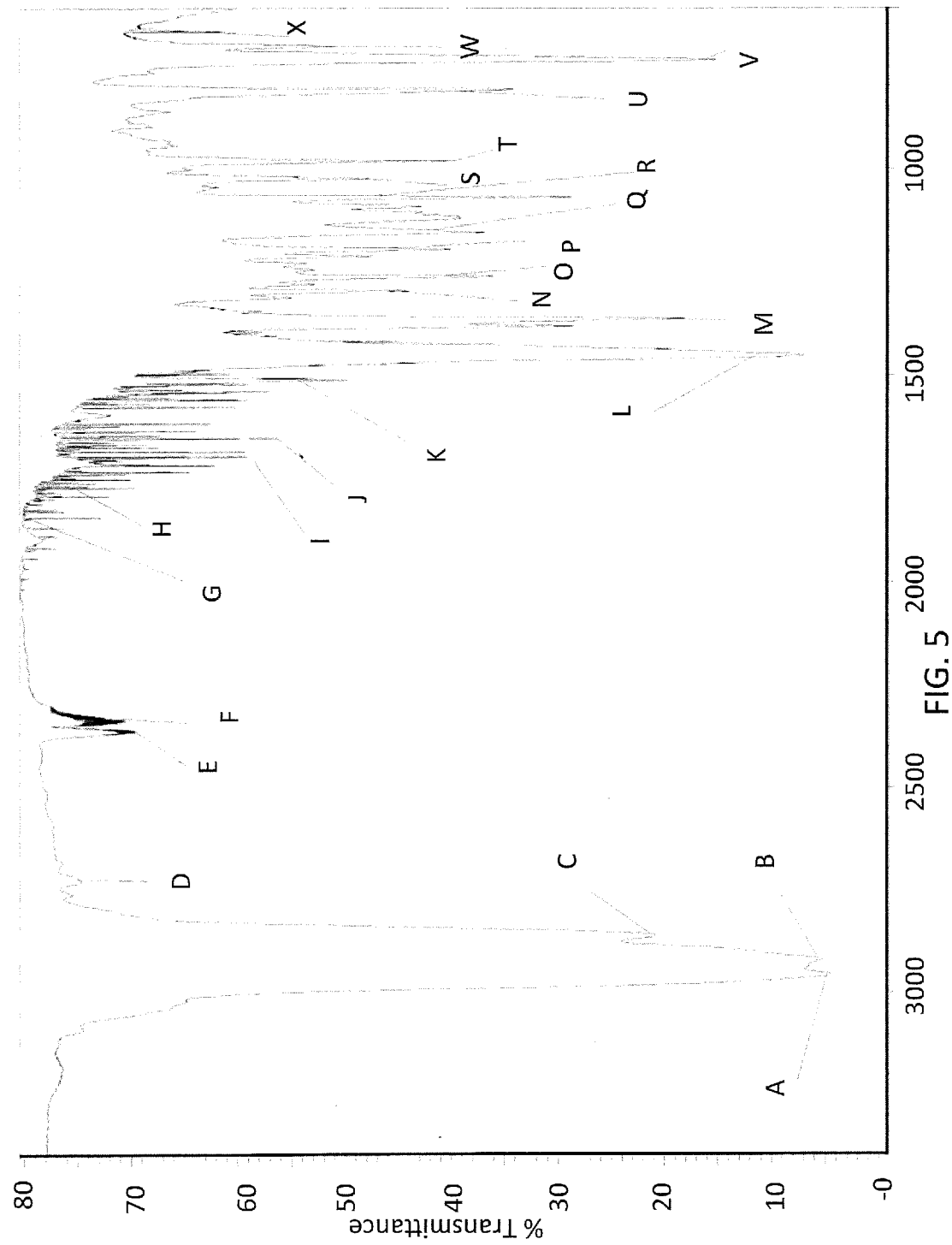
FIG. 5 is an IR spectrum of the polysulfide.
Figure 12:
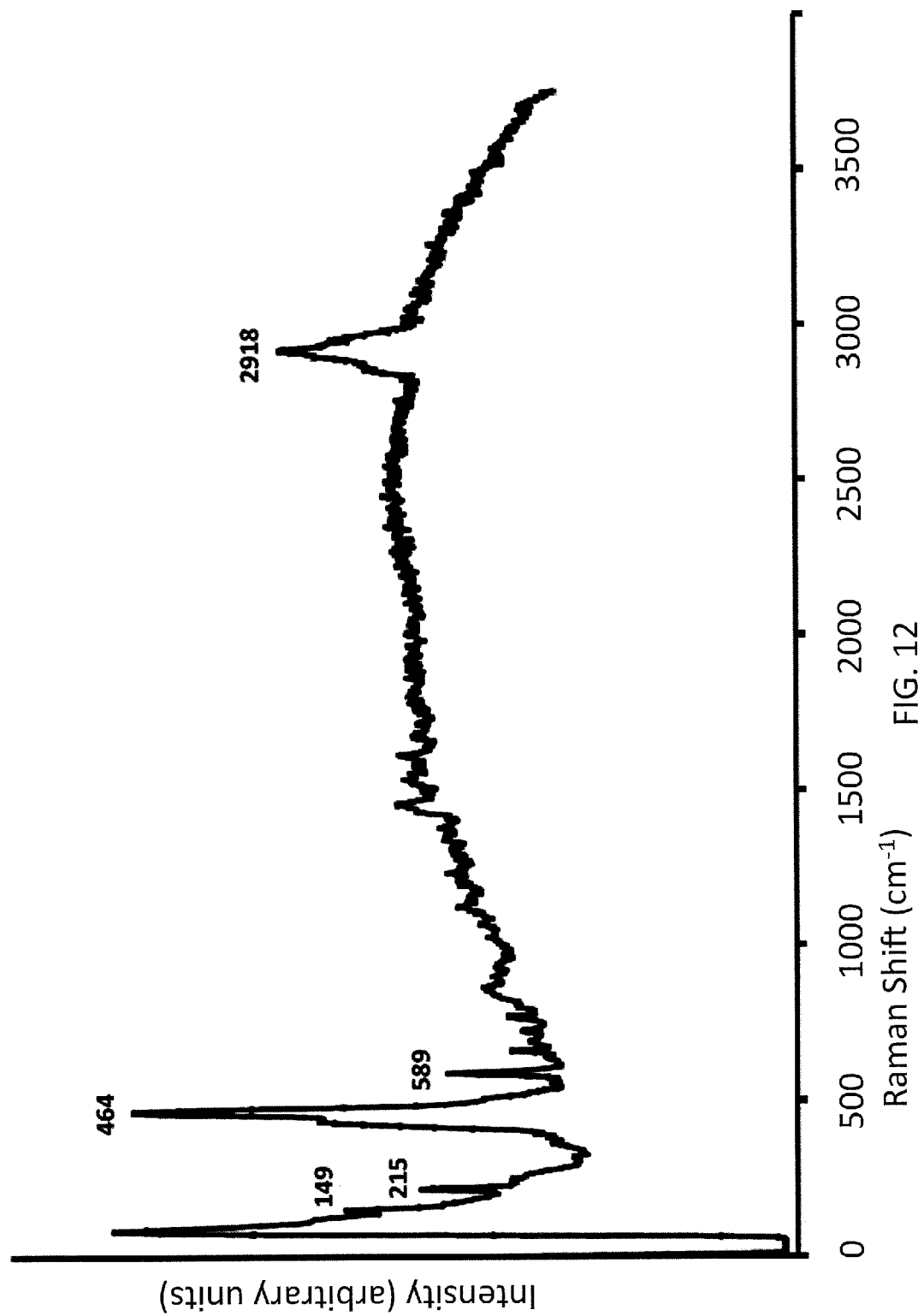
FIG. 12 depicts a Raman spectrum for the final sulfur-limonene polysulfide.

The IR scan of FIG. 5 indicates that the hydrocarbon framework of limonene is contained in the resulting polysulfide. To obtain the IR spectrum, several drops of the polysulfide were dissolved in CH$_2$Cl$_2$ (approx. 2 mg/mL), placed on a sodium chloride plate and dried. The resulting thin film was analyzed by FT-IR. The optical activity of the final product [α]D=−27.3 (c=1.0, CHCl$_3$) reflects the retention of at least a portion of the stereochemical integrity of the limonene domains in the resulting polymer. The optical measurement was taken using a polarimeter using the D-line of a sodium lamp, i.e. at 589 nanometer wavelength. The Raman spectra provided by FIG. 12 shows a distinct S—S peak at 464 cm$^{-1}$. The following table identifies the wavenumber for the peaks specifically identified in FIG. 5.

| Peak | Wavenumber |
| --- | --- |
| A | 2952.01 |
| B | 2916.34 |
| C | 2856.88 |
| D | 2722.12 |
| E | 2361.43 |
| F | 2329.72 |
| G | 1842.20 |
| H | 1770.86 |
| I | 1699.51 |
| J | 1651.95 |
| K | 1509.26 |
| L | 1445.84 |
| M | 1362.61 |
| N | 1295.23 |
| O | 1259.56 |
| P | 1192.17 |
| Q | 1148.57 |
| R | 1065.34 |
| S | 1025.70 |
| T | 982.10 |
| U | 815.63 |
| V | 736.36 |
| W | 704.65 |
| X | 661.05 |

Figure 6:
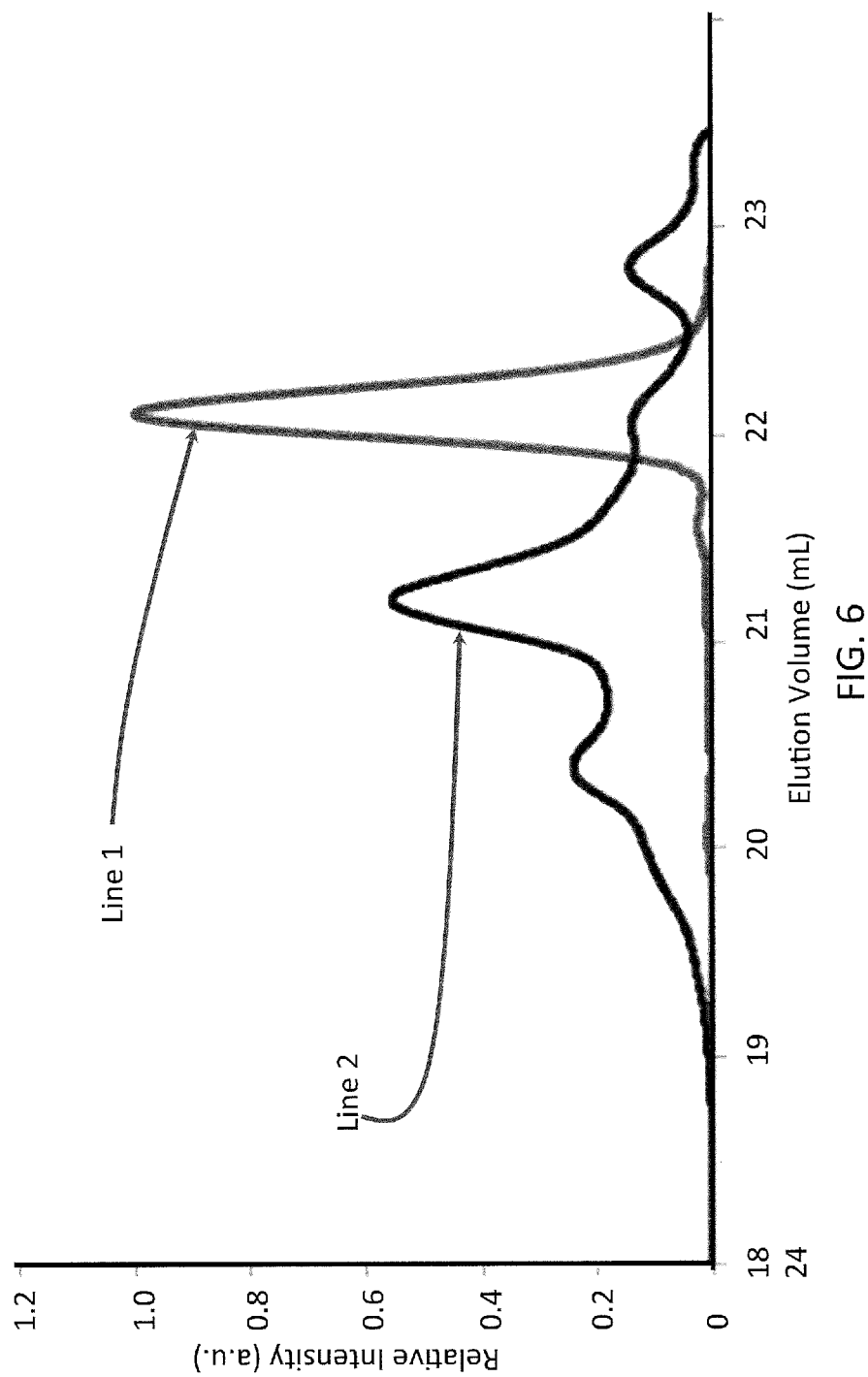
FIG. 6 is a graph of the size exclusion chromatography (SEC) analysis of the crude polysulfide prior to removal of unreacted or by-product volatile materials.
Figure 7:
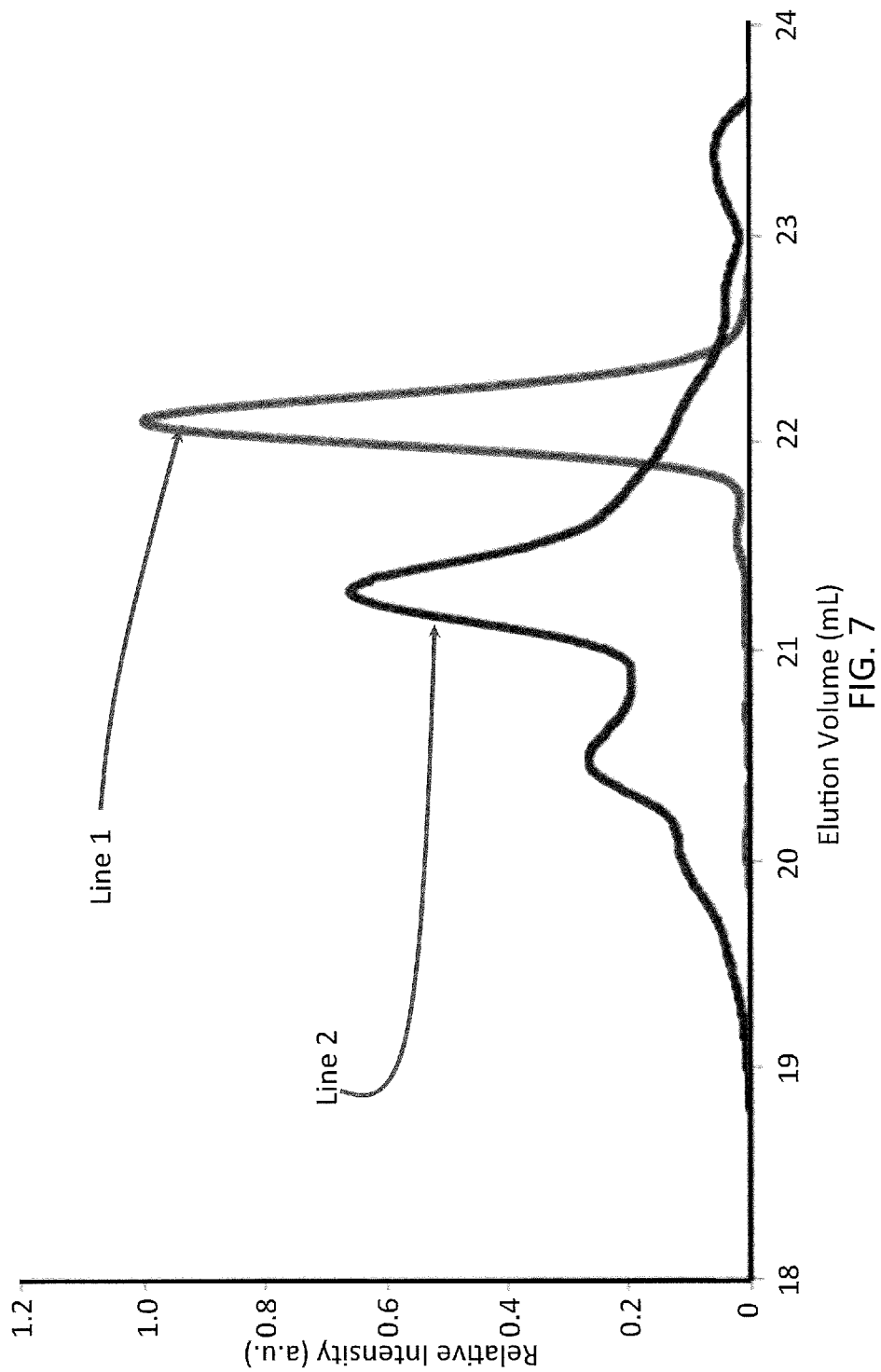
FIG. 7 is a graph of the SEC analysis of the refined polysulfide.
Figure 10:
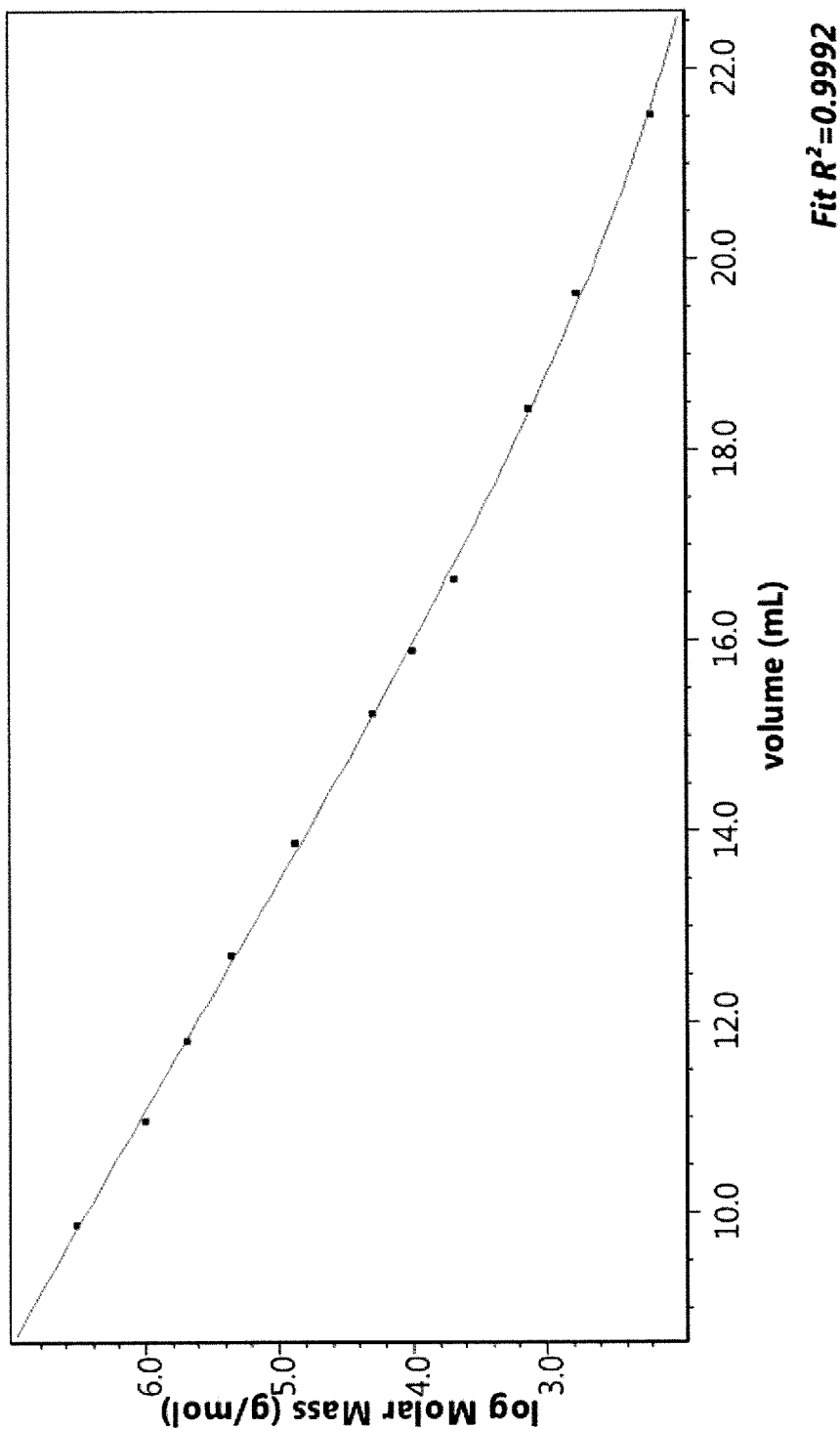
FIG. 10 depicts an SEC calibration curve using polystyrenes having molecular weights ranging from 162 Daltons to 3,242,000 Daltons.

The size exclusion chromatography (SEC) graphs of FIGS. 6 and 7 provide a basis for concluding that the resulting polysulfide has a number average molar mass ($M_n$) of 208.6, a mass average molar mass ($M_w$) of 244.9, and a Z-average molar mass of 298.8. The dispersity of the polysulfide ($M_w/M_n$) is 1.17. The values of FIGS. 6 and 7 are relative values because they were calculated based on a calibration curve for polystyrene as described herein. The SEC calibration curve of FIG. 10 represents molecular weights for a range of polystyrenes varying from 162 Daltons to 3,242,000. This data does not provide absolute molecular weight information (as the polysulfide elution profile was compared to styrene) and is primarily useful to calculate the polydispersity. Mass spectrometry (see next) was used to determine absolute molecular weights.

Figure 13:
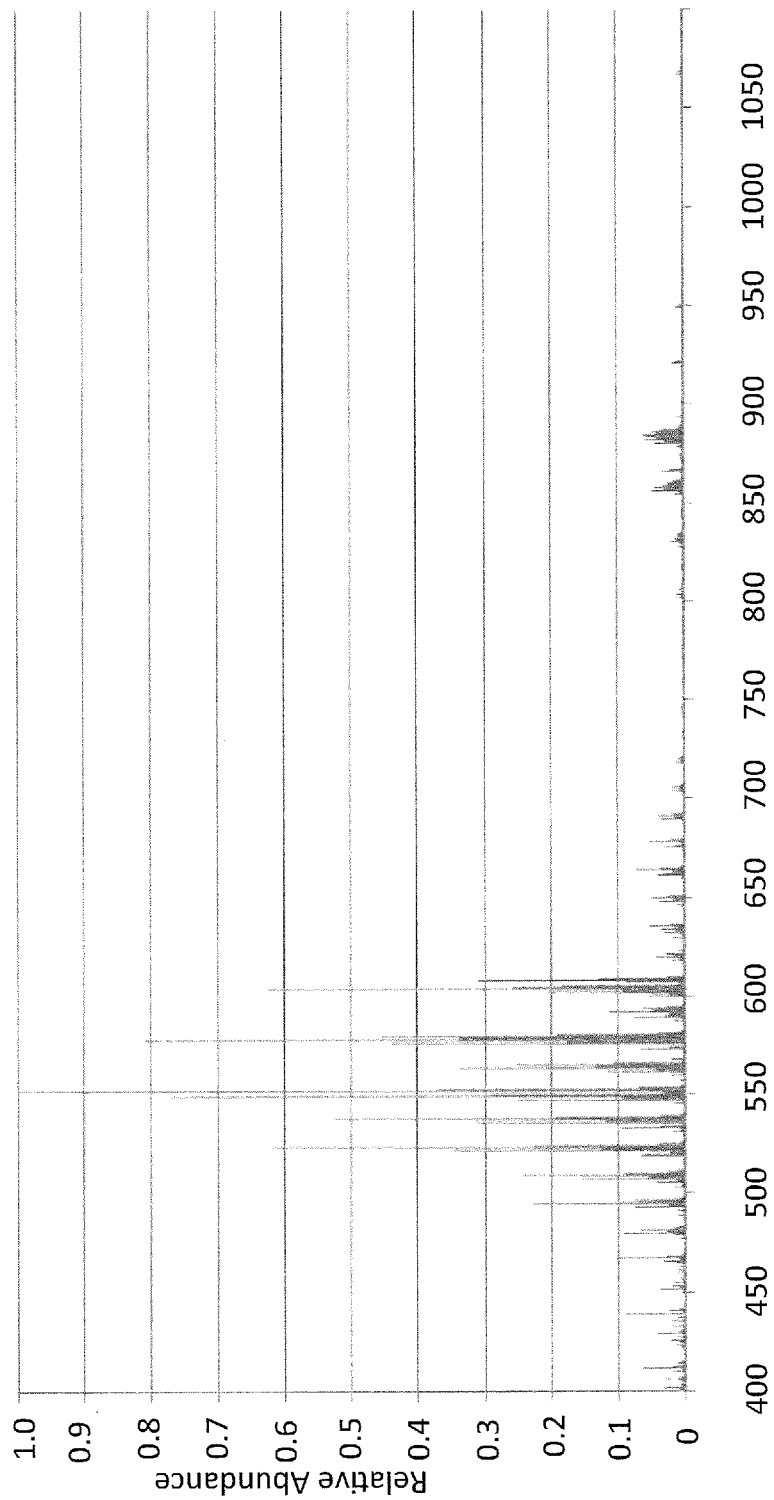
FIG. 13 depicts mass spectrometry results for the polysulfide using $Ag^+$ coordination.

Further analysis with mass spectrometry using Ag$^+$ coordination provided additional information about the molecular weight of the polysulfide. The Ag$^+$ coordination mass spectrum scan provided by FIG. 13, reflects a molecular weight in the range of 386 to 777 Da. Signals were detected from m/z=411 to m/z=949. These peaks correspond to the polysulfide components coordinated to a single Ag+ ion. The m/z therefore corresponds to [M+Ag]$^+$ where M is the molecular weight of the polysulfide component. Considering both mass spectrometry data and combustible analysis indicate that the polysulfide contains 1-3 limonene units and up to 19 atoms of sulfur. On average, the polysulfide contains 2 limonene units and 10 sulfur atoms with the following elemental composition: C, 38.97%; H, 4.97%; N, 0.0%; S, 56.60%. Key peaks from the mass spectral analysis provided by FIG. 13 are: m/z=495.4, 509.5, 521.5, 523.5, 537.5, 549.5, 551.5, 563.5, 565.5, 577.5, 579.5, 601.5, 603.5, 607.6, 619.6, 635.6, 649.6, 663.6, 677.6, 691.7, 705.7, 717.7, 731.7, 745.7, 749.7, 829.7, 855.8, 881.8, 886.8.

The following method was used to prepare the polysulfide for the Ag$^+$ coordination mass spectrum analysis. A 0.5 mg/mL solution of AgNO$_3$ in H$_2$O was prepared and mixed with methanol in a 9:1 ratio by volume to provide the mass spectrometry infusion solution. Subsequently, 20 mg of the polysulfide was added to the MeOH/H$_2$O/Ag$^+$ infusion solution to provide a saturated solution. A 100 microliter aliquot of the polysulfide saturated solution was further diluted to 1.0 mL with the MeOH/H2O/Ag$^+$ infusion solution to provide a final solution for mass spectrum analysis. The final solution was injected by direct infusion into the mass spectrometer using atmospheric pressure chemical ionization with operation in positive mode. A cluster of peaks was detected between m/z=495 and 886. Each of these peaks corresponds to a polysulfide molecule coordinated to a single silver ion, therefore the mass of the polysulfide detected in the mass spectrometer varies from approximately 386 to 777 Da. Note: two abundant isotopes of Ag$^+$ (106.9 and 108.9) results in a doublet for the [M+Ag]$^+$ that is separated by two mass units. In a control experiment without silver nitrate, a sample prepared by the same method gave no signal in the mass spectrometer.

Finally, the novel polysulfide disclosed herein does not readily oxidize. Rather, heating of the polysulfide to temperatures between about 200° C. and 300° C. will sever the sulfur-to-sulfur bonds of the polymer leading to depolymerization and resulting in volatile decomposition products. Thus, recovery of sequestered materials can be easily achieved by depolymerizing the polysulfide.

Figure 37:
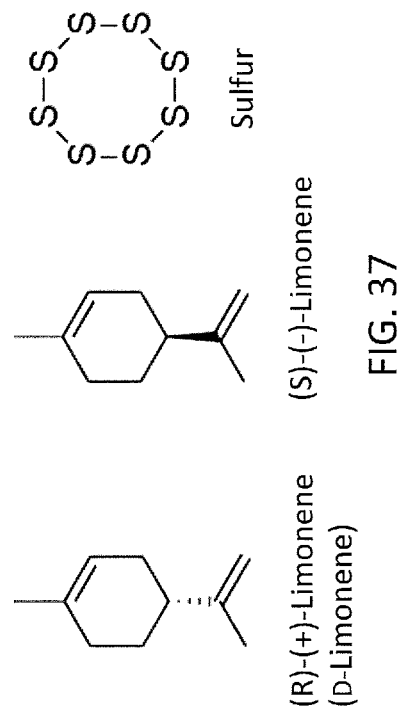
FIG. 37 depicts the structures of the reactants used to prepare the novel polysulfide.

The method for preparing the novel polysulfide advantageously utilizes industrial waste. The reactants used are limonene, either (R)-(+)-Limonene, also known as d-Limonene, or (S)-(−)-Limonene an enantiomeric form of d-Limonene and elemental sulfur. The structures of each enantiomer and elemental sulfur in the form of S$_8$ are shown in FIG. 37.

Typically, the raw materials will be treated to provide technical or analytical grade materials thereby enhancing the percent yield of the polysulfide and reducing the unreacted or waste material resulting from the polymerization reaction. However, the following method will consistently produce the desired polysulfide independent of whether the starting materials are industrial grade, technical grade or analytical grade.

In general, the method for preparing the above described polysulfide entails initially adding sulfur to a reactor and heating the sulfur sufficiently to melt the sulfur. Typically, heating sulfur to a temperature between about 115° C. to about 130° C., preferably of about 120° C. to about 124° C., at atmospheric pressure will be sufficient to melt the sulfur. Preferably, some form of agitation will be provided to ensure even and consistent melting of the sulfur. The reactor can be glass, ceramic, or stainless steel open to the atmosphere but provided with an extractor vent to remove any volatile materials.

Following melting of the sulfur, a mass of limonene is added to the molten sulfur and the temperature of the reactor increased. Limonene suitable for use in this method may be (R)-(+)-Limonene, also known as d-Limonene, or (S)-(−)-Limonene an enantiomeric form of d-Limonene and mixtures thereof. As noted above any reference to limonene herein refers to either enantiomer and mixtures thereof. Upon addition of the limonene, a two-phase mixture results. The two-phase mixture is heated to a temperature between about 130° C. and 200° C.; however, when operating at temperatures above the 176° C. boiling point of limonene the reaction must take place under increased pressure and/or a reflux system to preclude unnecessary loss of limonene. The reaction continues until a single phase is present in the reactor. Typically, the reaction step will occur at temperature between about 160° C. and 175° C. Preferably, the mixture will be heated at a temperature of about 170° C. for a time period sufficient to yield a single-phase. Depending upon reactor size and operating temperature, the reaction step may take from about 30 minutes to about two hours. In general, as noted above, formation of a single phase within the reactor signals the termination of the reaction step as the single phase comprises the desired sulfur-limonene polysulfide, referred to herein as polysulfide. As noted below, some side reactions occur requiring further purification to yield predominately the desired polysulfide.

Figure 38:
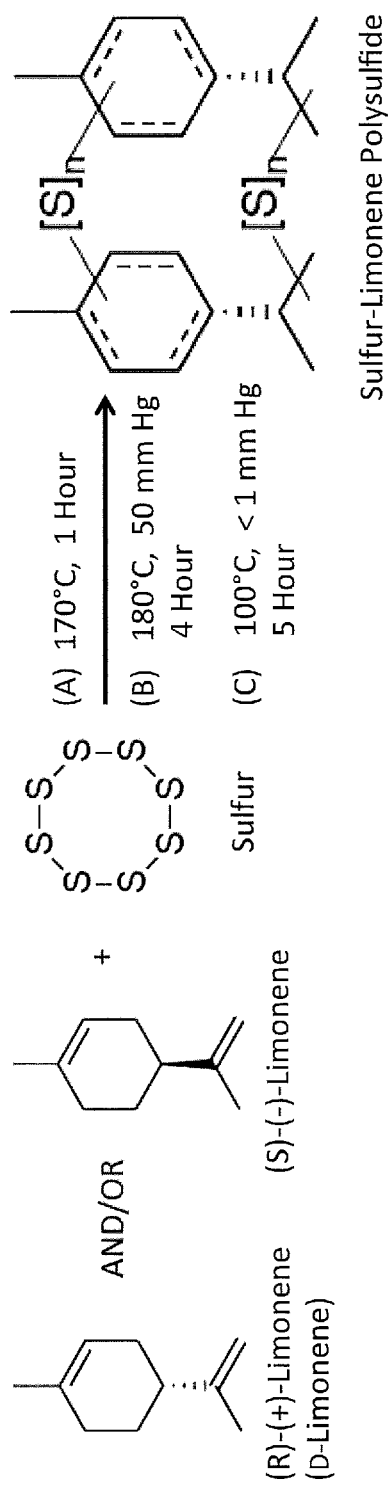
FIG. 38 depicts the generic reaction process.
Figure 39:
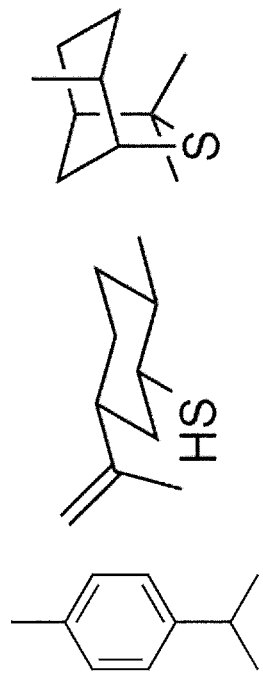
FIG. 39 depicts volatile by-products of the reaction between limonene and sulfur.
Figure 41:
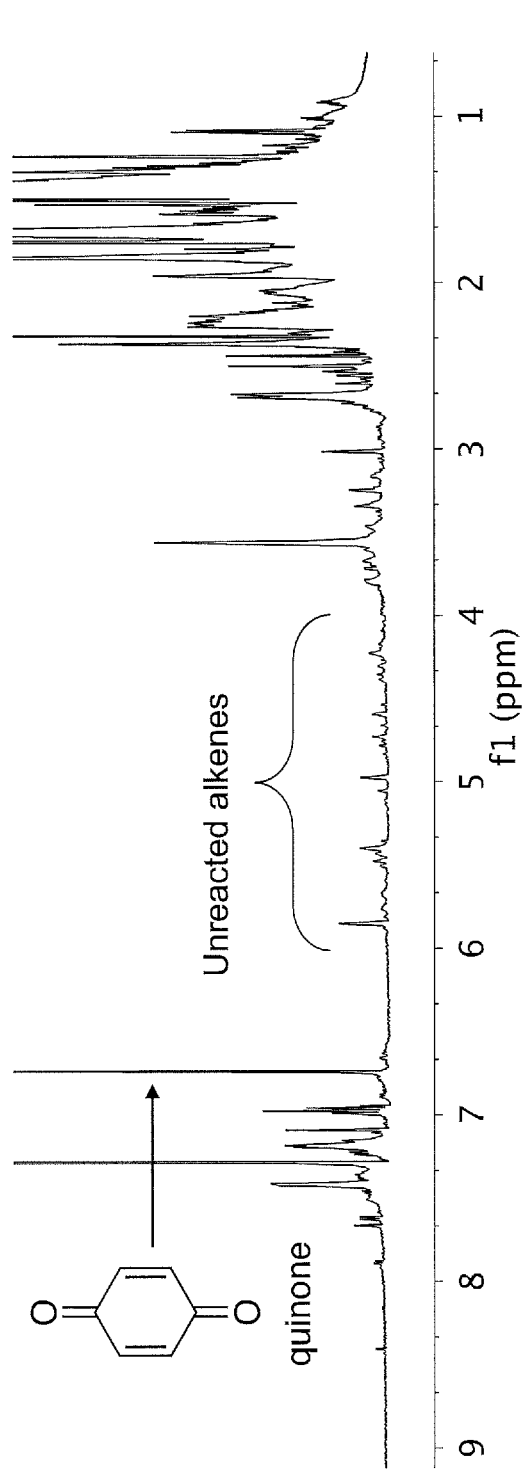
FIG. 41 depicts a $^1$H NMR (600 MHz) scan of the reactants when a radical inhibitor is included in the reaction mixture.
Figure 42:
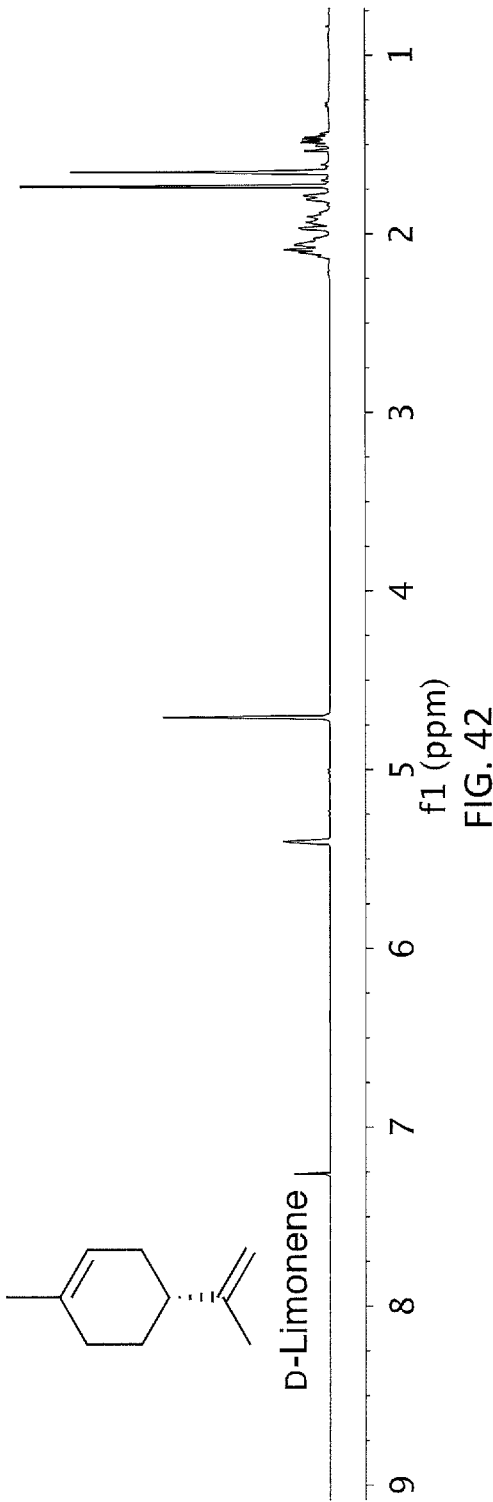
FIG. 42 is a $^1$H NMR (600 MHz) scan of limonene.

One alternative reaction condition includes heating the two phase mixture to a temperature of about 176° C. to about 185° C., preferably 180° C., under a reduced pressure of about 45 mm Hg (6.0 kPa) to about 55 mm Hg (7.3 kPa), preferably 50 mm Hg (6.7 kPa), as measured with a manometer, for about three to about five hours, preferably four hours. Another alternative reaction condition heats the two phase mixture to a temperature of about 90° C. to about 110° C., preferably 100° C., at a pressure of less than 1 mm Hg (0.13 kPa) for a period of about four hours to about six hours, preferably five hours. The reactions are schematically depicted by FIG. 38. The reaction is believed to proceed by a radical mechanism. To test this theory, the reaction process was repeated using 500 mg of sulfur. Following heating of the sulfur, 50 mg of hydroquinone was added to the sulfur prior to addition of 500 mg of limonene. The mixture was stirred for 15 minutes at 170° C. followed by addition of 50 mg hydroquinone. The mixture was maintained at 170° C. for an additional 105 minutes. Analysis of the mixture after cooling indicated only partial reaction of limonene. The final solution was analyzed using $^1$H NMR (600 MHz). As reflected in FIG. 41, the NMR peaks indicate the presence of alkenes associated with partially reacted limonene and p-benzoquinone. The formation of p-benzoquinone is consistent with hydroquinone acting as an H-atom donor thereby terminating radical intermediates. FIG. 42 is a $^1$H NMR (600 MHz) scan of limonene. Comparison of FIGS. 41 and 42 indicates that the radical inhibitor precluded the formation of the polysulfide.

Upon completion of the reaction, the single-phase mixture is allowed to cool to room temperature. Volatile by-products may also be present along with the resulting polysulfide. These components, typically p-cymene and low molecular weight thiols and sulfides, can be removed by evaporation at 25° C. to 100° C., distillation or vacuum distillation. Vacuum distillation will take place at about 100° C. to about 180° C. under a vacuum of about <1 mbar (0.1 kPa) to 100 mbar (10 kPa) for about one to ten hours until substantially all volatile material is removed from the polysulfide. An optional vacuum distillation step occurring at 100° C. and less than 1 mm Hg (0.13 kPa) for three to six hours may be applied. Note: the removal of volatile by-products may be carried out prior to allowing the single-phase mixture to cool to room temperature or after allowing the single phase mixture to cool to room temperature.

Figure 11:
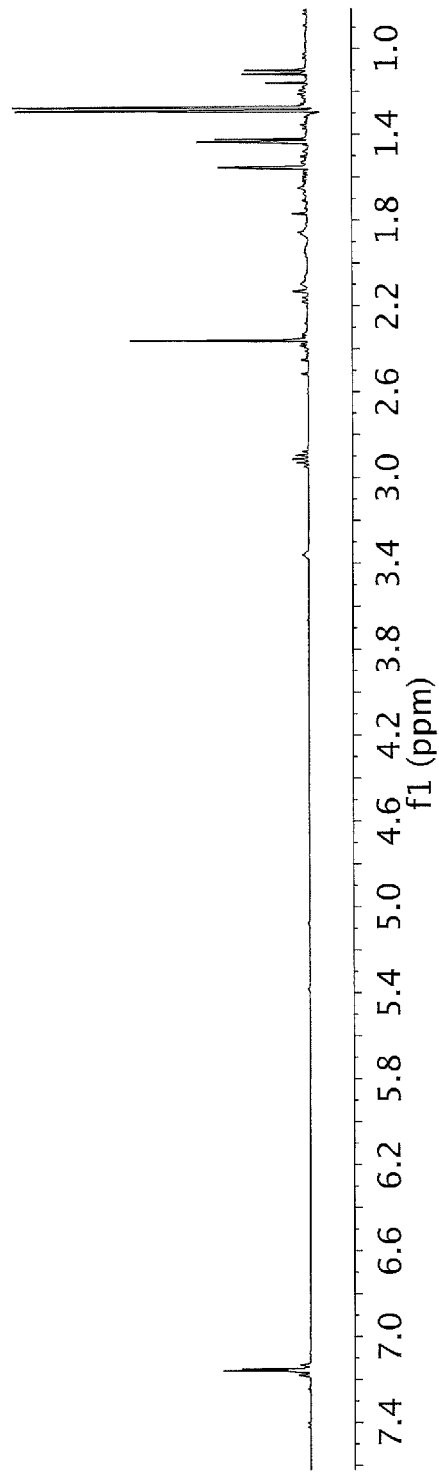
FIG. 11 depicts the $^1$H NMR for the volatile byproducts produced by the method described herein. The major product of the volatile material is p-cyrnene with signals at 7.15-7.16 ppm (4H, m, ArH), 2.88-2.95 ppm (1H, sept., $CHMe_2$), 2.3 ppm (3H, s, CH3) and 1.28 ppm (6H, d, $CHMe_2$).

Following removal of the volatile components, the overall method typically results in a yield of the desired limonene-polysulfide of about 70% to 90% of the theoretical yield. As noted above, the final polysulfide is a transparent, red solid. FIG. 11 depicts a $^1$H NMR (400 MHz, $CDCl_3$) of the volatile byproducts isolated by the distillation step. The scan corresponds to the presence of p-cymene and other volatile sulfides and thiols. Representative peaks associated with the volatile compounds as depicted in FIG. 11 are found at: 7.16, 7.15, 3.37, 3.36, 3.35, 2.95, 2.93, 2.91, 2.90, 2.88, 2.52, 2.38, 2.18, 2.13, 2.06, 1.86, 1.77, 1.55, 1.43, 1.42, 1.29, 1.27, 1.16, 1.12, 1.10.

Typically, the method for preparing the polysulfide will follow these steps. Heat the elemental sulfur to a temperature sufficient to melt the sulfur. As discussed above, the sulfur will generally be heated with stirring or agitation to about 120° C. to about 124° C. at atmospheric pressure. A wide range of ratios of limonene to sulfur will perform satisfactorily for the method of producing the polysulfide. In general, the mass ratio of limonene/sulfur may range from 1:1.5 to 1.5:1. Preferably, the ratio of limonene to sulfur will be 1:1. The ratio of limonene to sulfur is selected to provide a reaction product, polysulfide and volatiles, that is at least 70% polysulfide by weight. More preferably, the reaction product, polysulfide and volatiles, is at least 80% polysulfide by weight. Additionally, the reaction product is substantially free of unreacted sulfur. Typically, the products will have less than 4% unreacted sulfur by weight.

Following addition of the limonene to the molten sulfur, the resulting two-phase mixture is heated to a temperature between about 130° C. and 200° C. Generally, the reaction time required to provide a single phase of the resulting polysulfide will be about 30 minutes to about two hours. Optionally, to remove volatile by-products from the polysulfide, the single-phase product is heated at a temperature greater than the vaporization point of the probable by-products. Alternatively, vacuum distillation performed under the appropriate temperatures as determined by the probable by-products may be used to remove the unwanted by-products. The final polysulfide is stable up to 200° C. and decomposes at temperatures above 200° C. Objects formed from the polysulfide will retain their shape at temperatures between 4° C. and 60° C.

Figure 9:
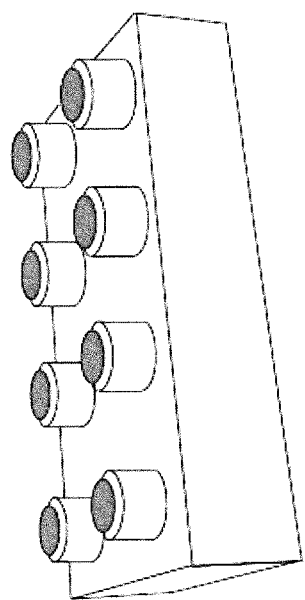
FIG. 9 depicts a molded object formed from the polysulfide.

The resulting polysulfide has thermoplastic characteristics. Thus, the polysulfide may be formed into objects using conventional techniques suitable for thermoplastic polymers including but not limited to injection molding and spin casting. As depicted in FIG. 9, a material formed by pouring the liquid polysulfide into a mold will retain its shape after cooling. When applied as a spun coated material, the vacuum distillation steps may be optionally omitted from the method of preparing the polysulfide as retained volatile components will aid in the plasticization of the polymer during the coating process and evenness of the resulting polysulfide coating. Additionally, the temperatures used during the coating process will subsequently drive off the retained volatile components such as p-cymene. Thus, spin coating forms an object from the polysulfide and removes volatile by-products in a single step. As used herein, a polysulfide object may take any form as prepared by any suitable process. As noted above, thermoplastic molding techniques, including spin molding, may be used to design a variety of useful objects suitable for carrying out the contemplated use of sequestering palladium and mercury commonly found as environmental contaminants. Non-limiting examples may include objects spun coated on the interior of pipes or injection molded into lattice type nets. Preferably, the manufacturing process provides a polysulfide object having a large surface area thereby enhancing the ability of the polysulfide to sequester palladium and mercury.

Figure 14:
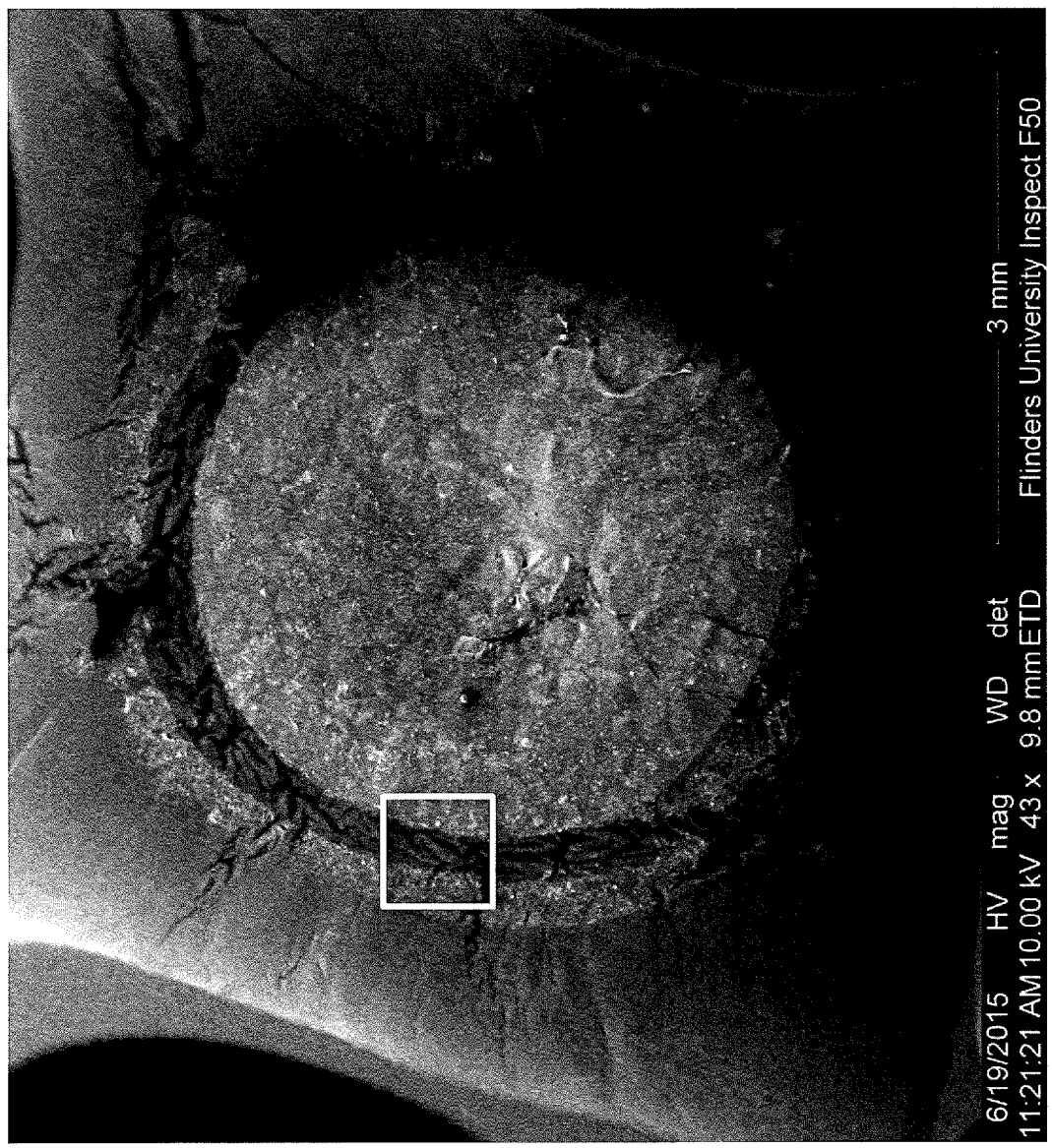
FIGS. 14-17 are scanning electron microscope images of the surface of the polysulfide after exposure to $HgCl_2$.
Figure 15:
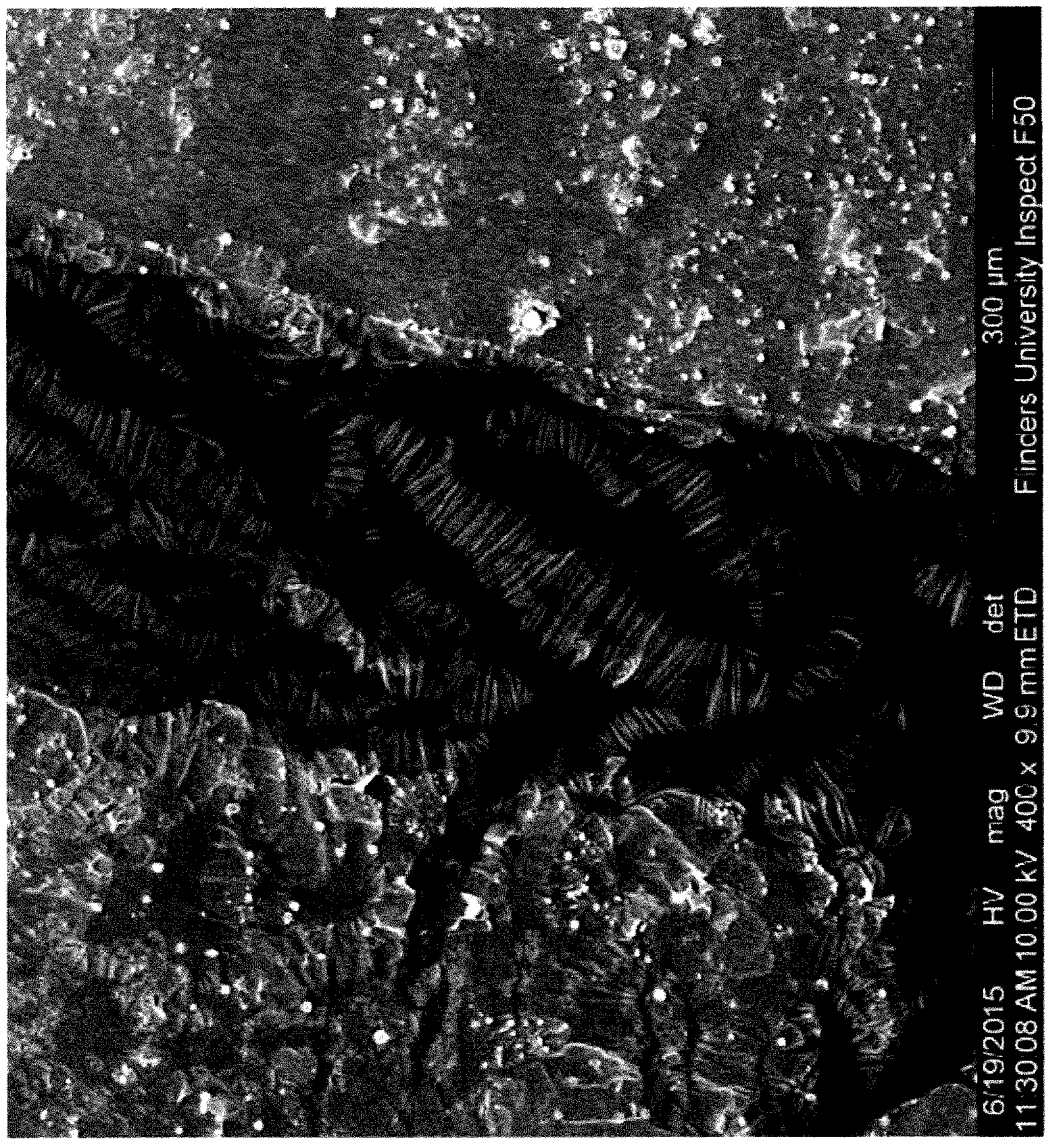
Figure 16:
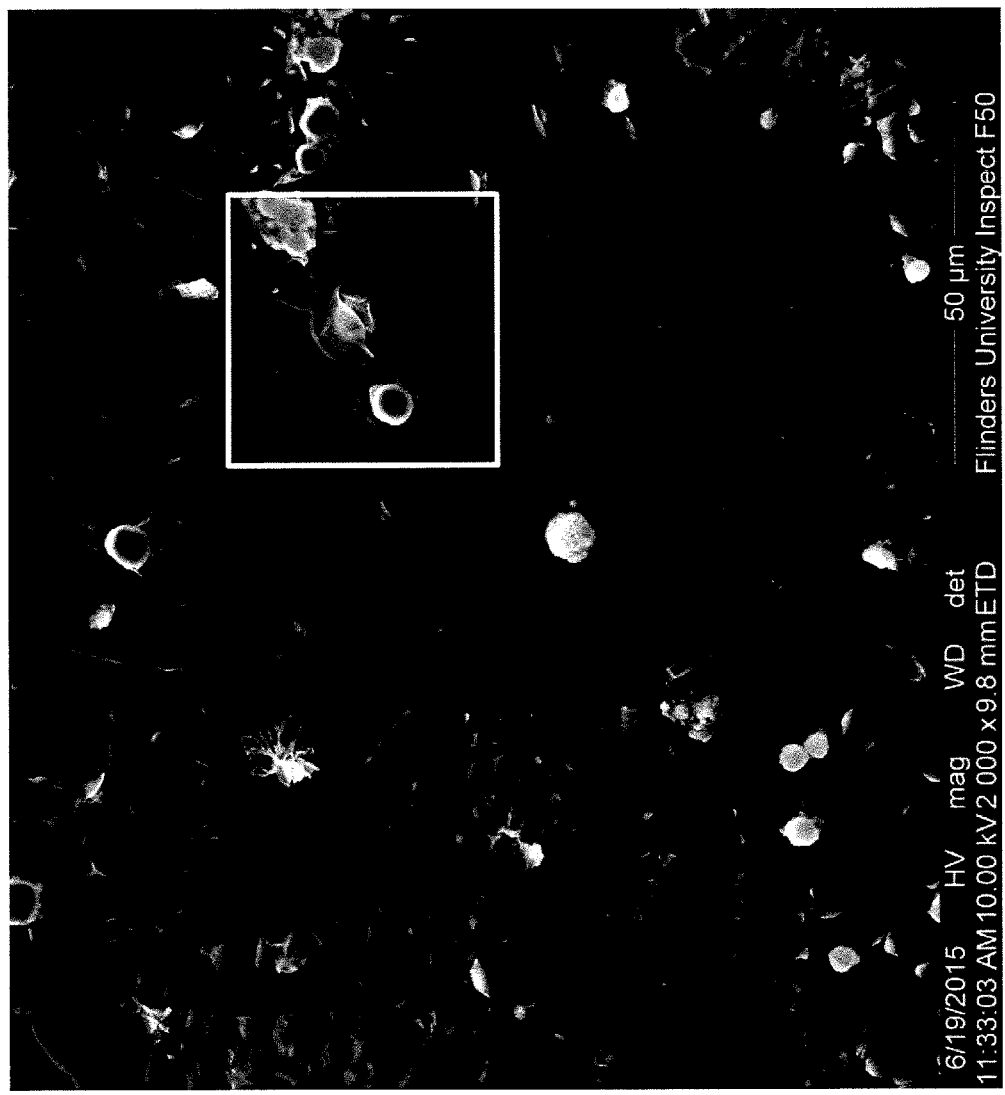
Figure 17:
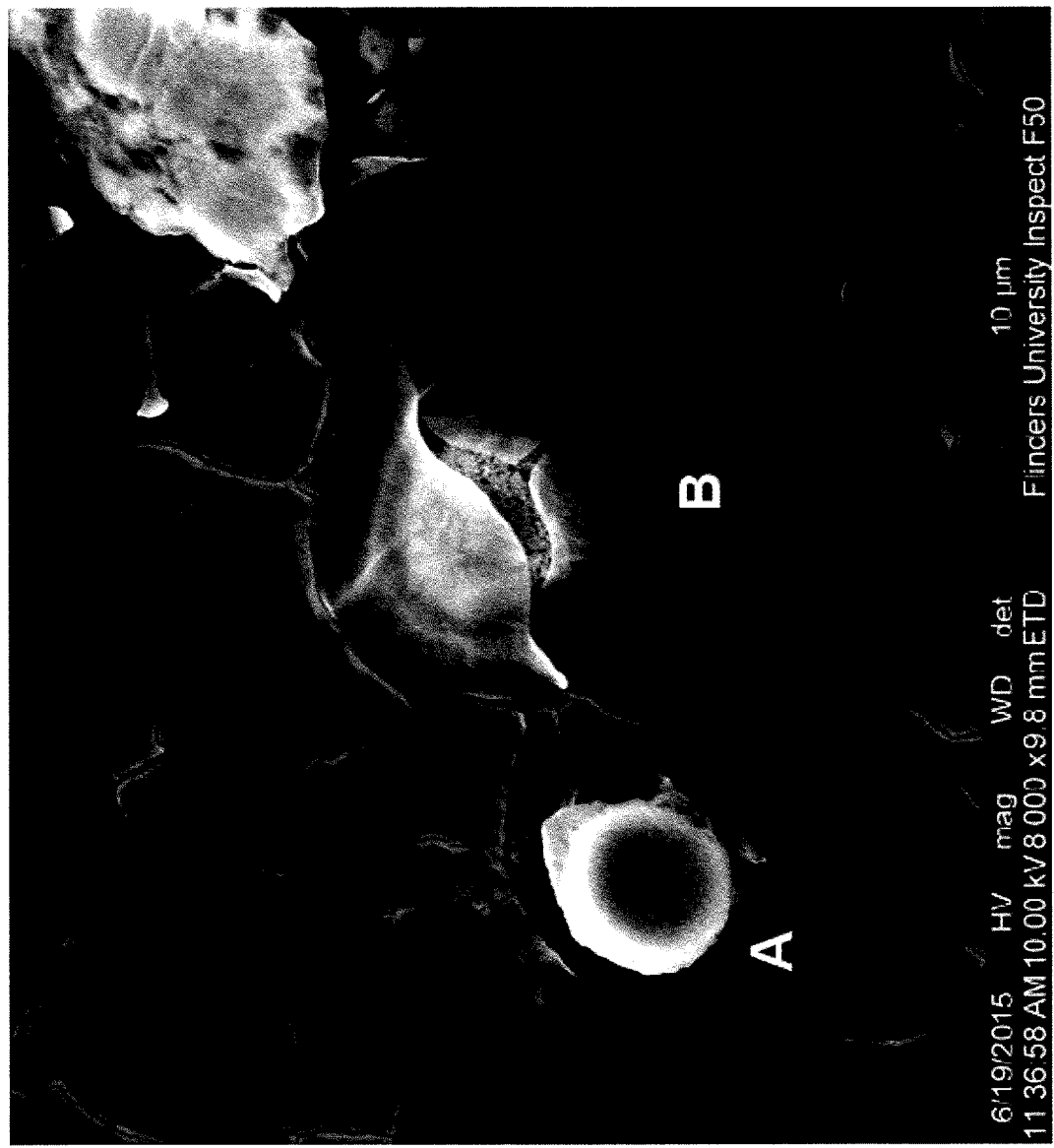

FIGS. 14-35 provide further classification and understanding of the binding of mercury (II) to the polysulfide. FIG. 14 depicts the surface of the polysulfide following application of a drop of $HgCl_2$ as a 10 mM solution. As depicted, the circular area corresponds to the drop of the solution. FIG. 15 focuses on the identification box in FIG. 14. FIG. 15 reflects the demarcation area between the surface of polysulfide exposed to a solution of $HgCl_2$ and the region that has not been exposed to $HgCl_2$. FIG. 16 provides an enlarged view of the surface of the polysulfide following exposure to $HgCl_2$. As depicted therein, following exposure of the polysulfide to $HgCl_2$ micro- and nano-particles in the form of a mercuric sulfide form and adhere to the surface of the polysulfide. The region, containing the micro- and nano-particles of mercuric sulfide, corresponds to the observed color change from red to yellow. FIG. 17 is an enlargement of the identification box depicted in FIG. 16. As depicted in FIG. 17, the mercuric particles, as micro- and nano-particles, not only adhere to the surface (area A) of the polysulfide but may also become enveloped by the polysulfide and sink partially beneath the surface (area B) of the polysulfide.

Figure 18:
FIGS. 18-19 are scanning electron microscope images or regions analyzed by energy dispersive x-ray of the polysulfide.
Figure 19:
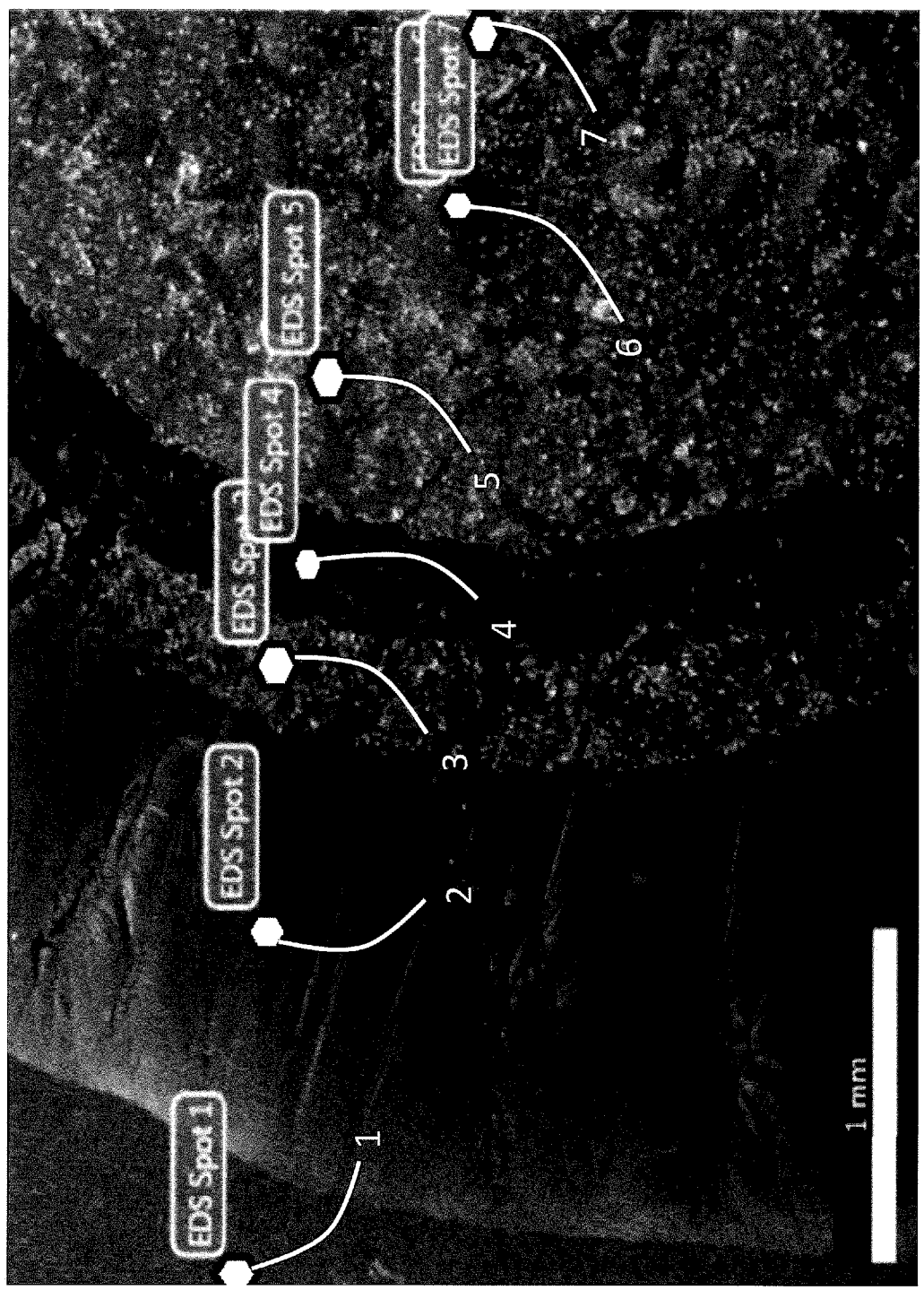
Figure 20:
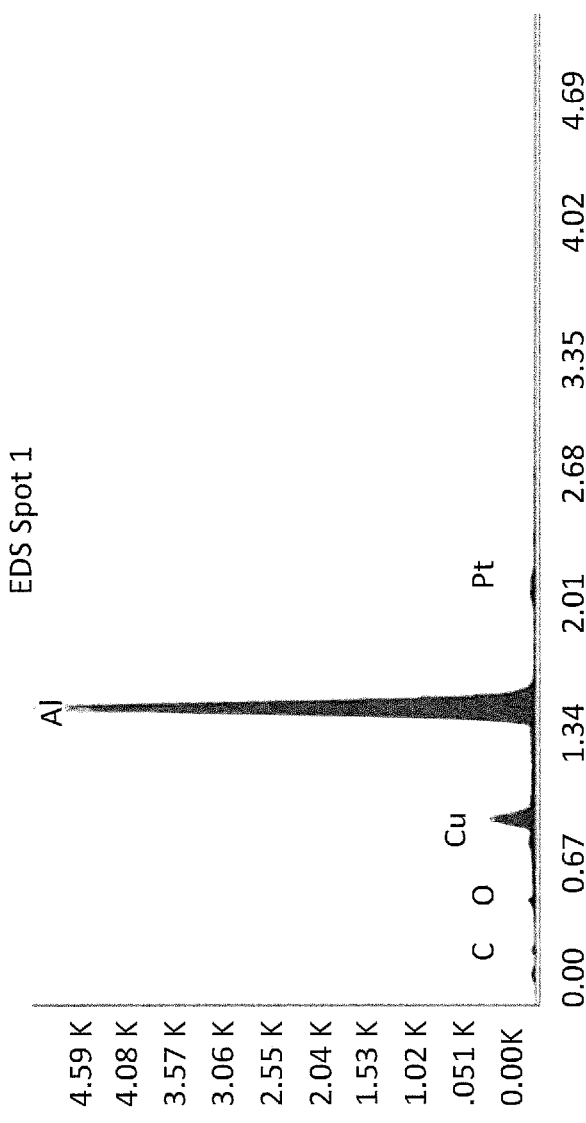
FIG. 20-26 are the scans produced by the energy dispersive x-ray analysis for each spot identified in FIG. 19.
Figure 21:
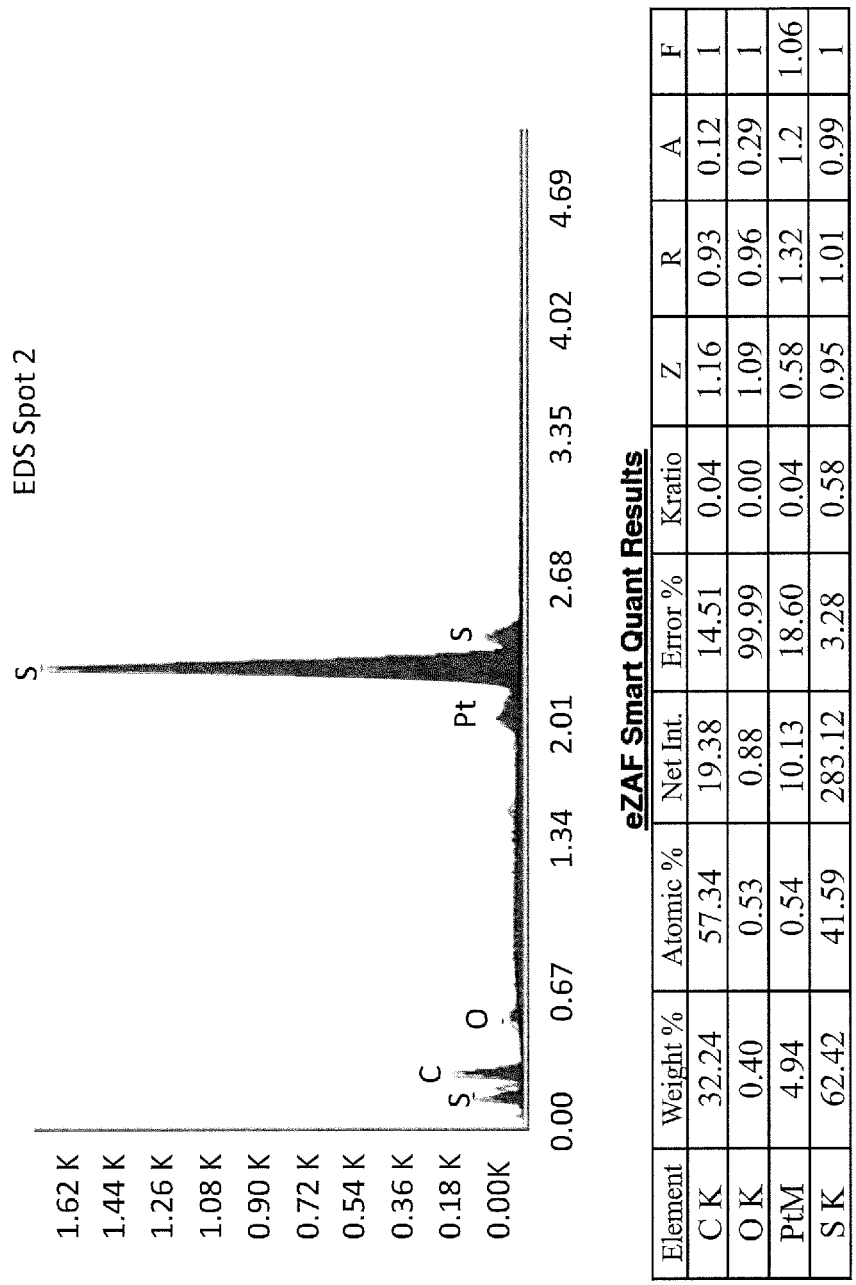
Figure 22:
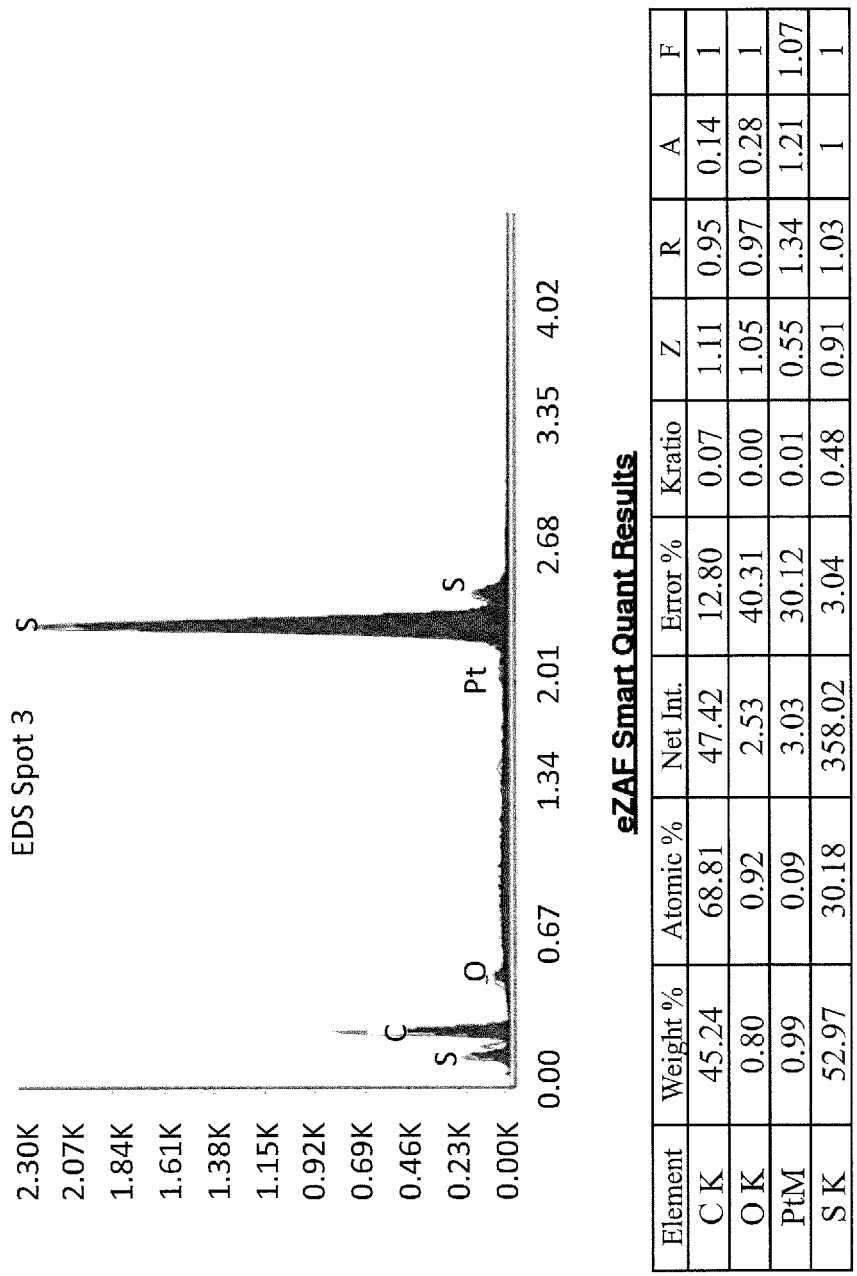
Figure 23:
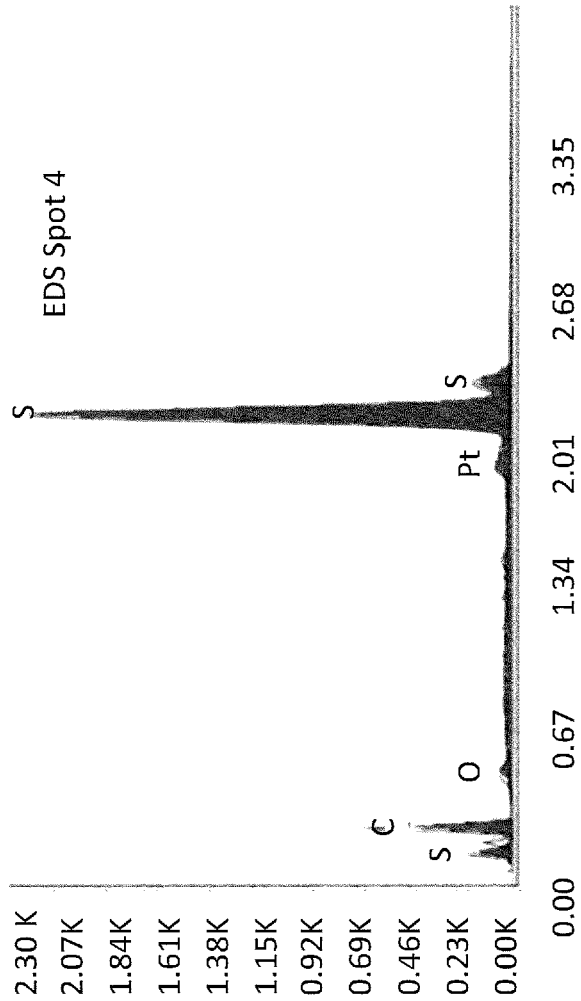
Figure 24:
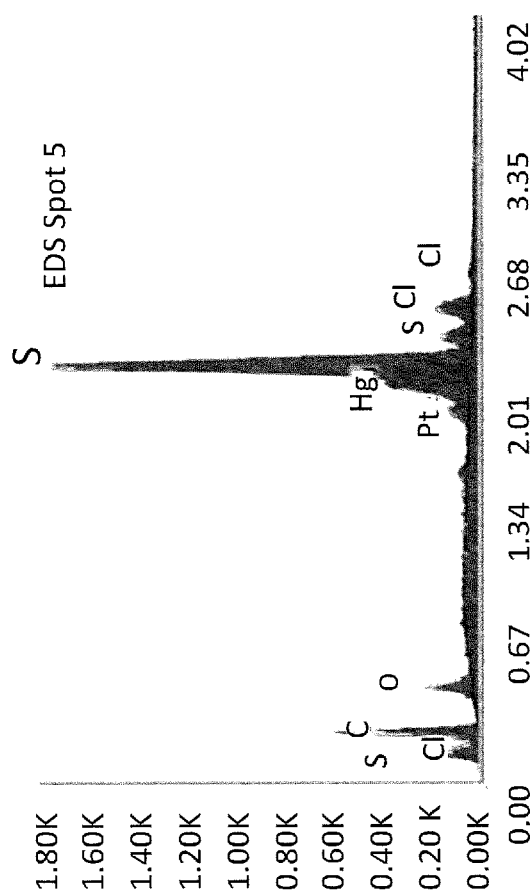
Figure 25:
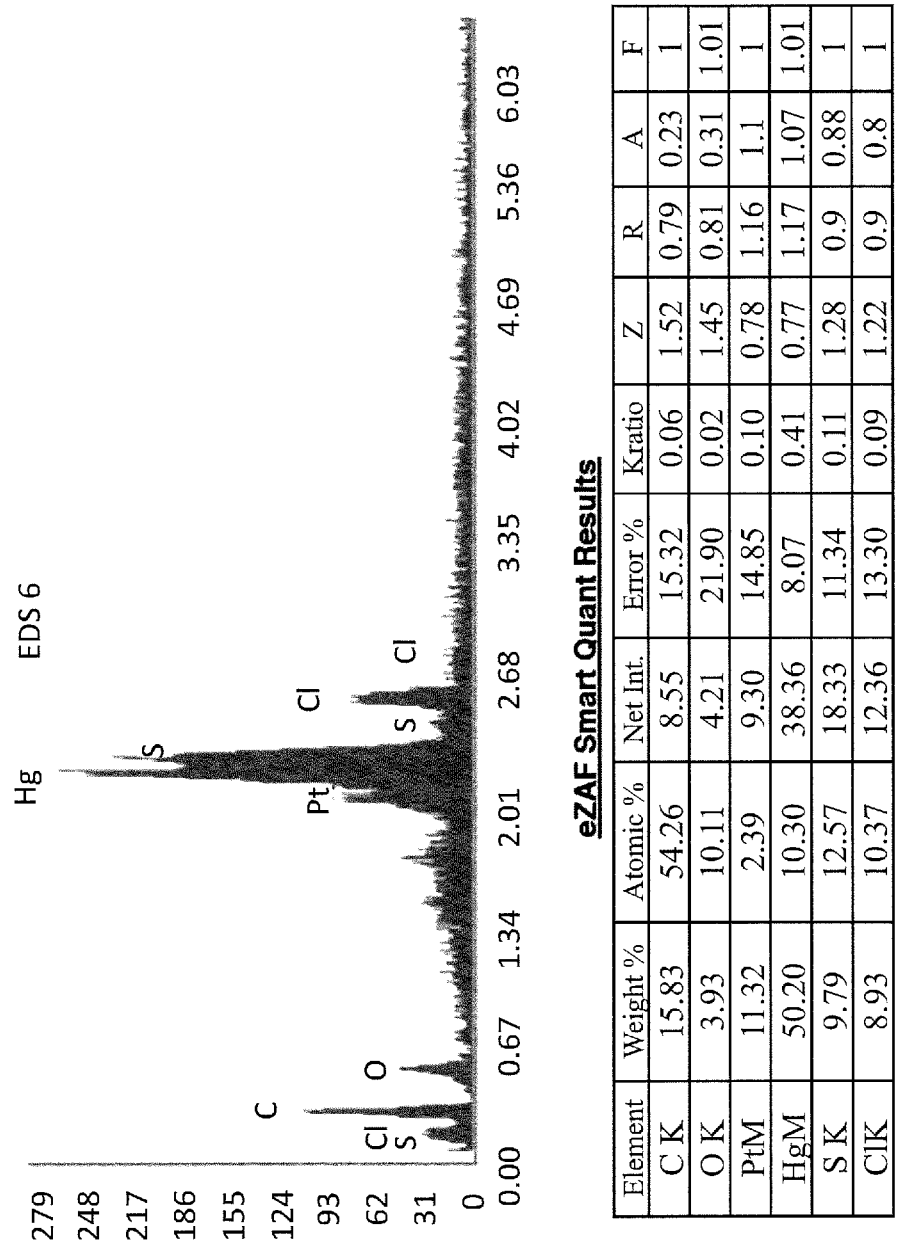
Figure 26:
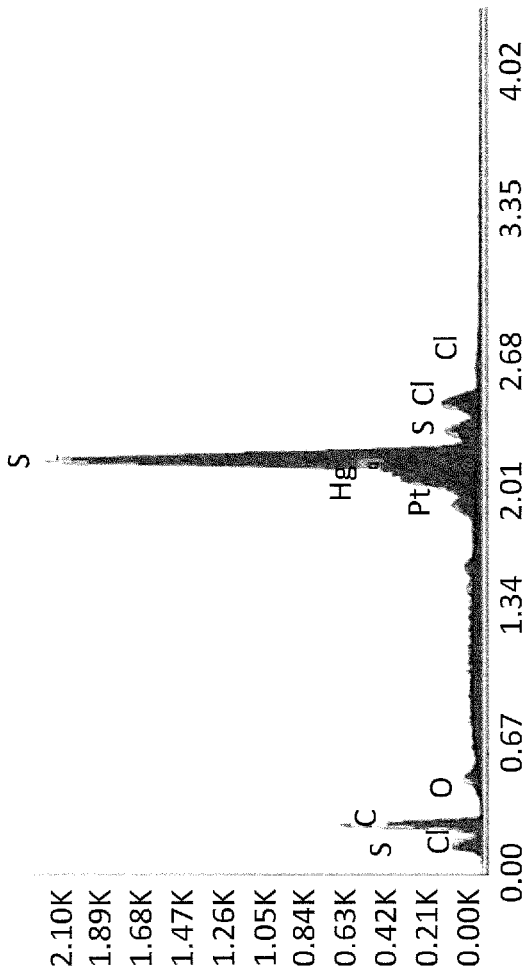

FIGS. 18-19 provide scanning electron microscope images of a polysulfide following exposure to $HgCl_2$ and after formation of the micro- and nano-particles of mercuric sulfide. Each identified location in FIG. 19 has been analyzed using energy dispersive x-ray spectroscopy (EDS, also known as EDX). FIGS. 20-26 provide the results of the EDS analysis for each spot, EDS 1-EDS 7 respectively. EDS spot 1 (FIG. 20) is a control region that lacks polysulfide and lacks $HgCl_2$. The resulting scan reflects the detection of aluminum in the SEM sample holder. EDS 2 (FIG. 21) is a second control that contains the polysulfide that was not exposed to the $HgCl_2$. As reflected in FIG. 21, the SEM produced a peaks corresponding to the sulfur and carbon components of the polysulfide. EDS spots 3 and 4 are on the border of the region exposed to. $HgCl_2$. As depicted in FIGS. 22-23, EDS spots 3 and 4 lack any elements corresponding to $HgCl_2$; therefore, EDS spots 3 and 4 were not exposed to $HgCl_2$. In contrast, EDS spot 5 clearly lies within the region exposed to $HgCl_2$. The presence of mercury was confirmed by the SEM analysis depicted in FIG. 24. Based on the SEM and EDS analysis, this region of the scan had 17% mercury by weight. EDS spot 6 corresponds to spot A in FIG. 17. The SEM and EDS analysis depicted in FIG. 25 reflects the higher concentration (50 weight %) of mercury in the resulting particle. Further, the SEM analysis of the particle reflects an atomic ratio of sulfur to mercury of 10.4 to 12.6, a ratio consistent with a mercury sulfide particle. In contrast to FIG. 25, FIG. 26 depicts the SEM results for an area exposed to $HgCl_2$ and adjacent to a mercuric sulfide particle. As depicts in FIG. 26, the polysulfide carries adhered mercury; however, the mercury has not formed a micro- or nano-particle. Thus, mercury may bind to the polysulfide without undergoing conversion to a mercuric sulfide particle.

Figure 27:
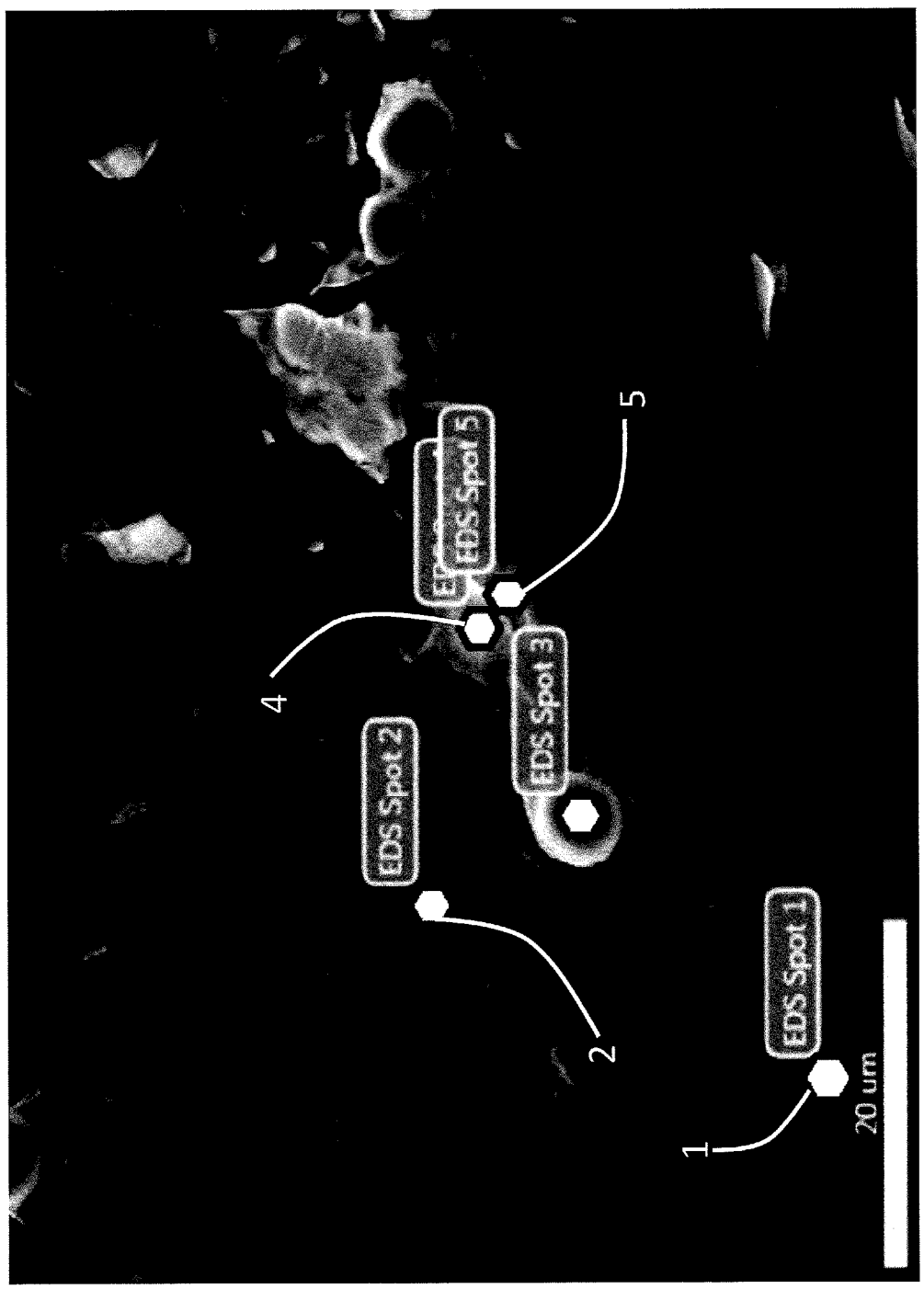
FIG. 27 is an enlargement of the scanning electron microscope image of FIG. 16.
Figure 28:
FIG. 28 is an enlargement of the area identified as EDS Spot 3 with the identified region in the box in FIG. 27.
Figure 29:
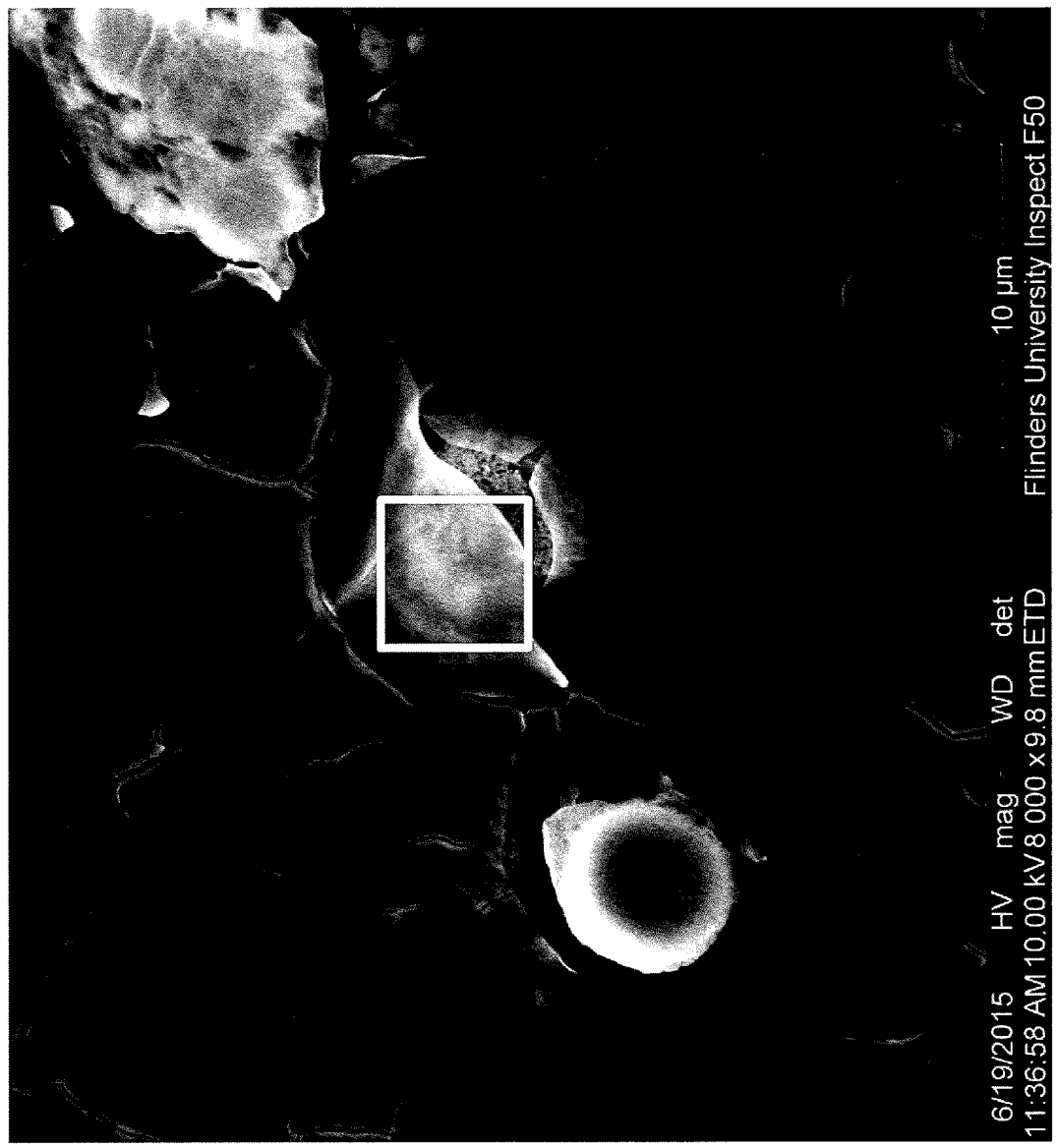
FIG. 29 is an enlargement of the area identified as EDS Spot 4 with the identified region in the box in FIG. 27.
Figure 30:
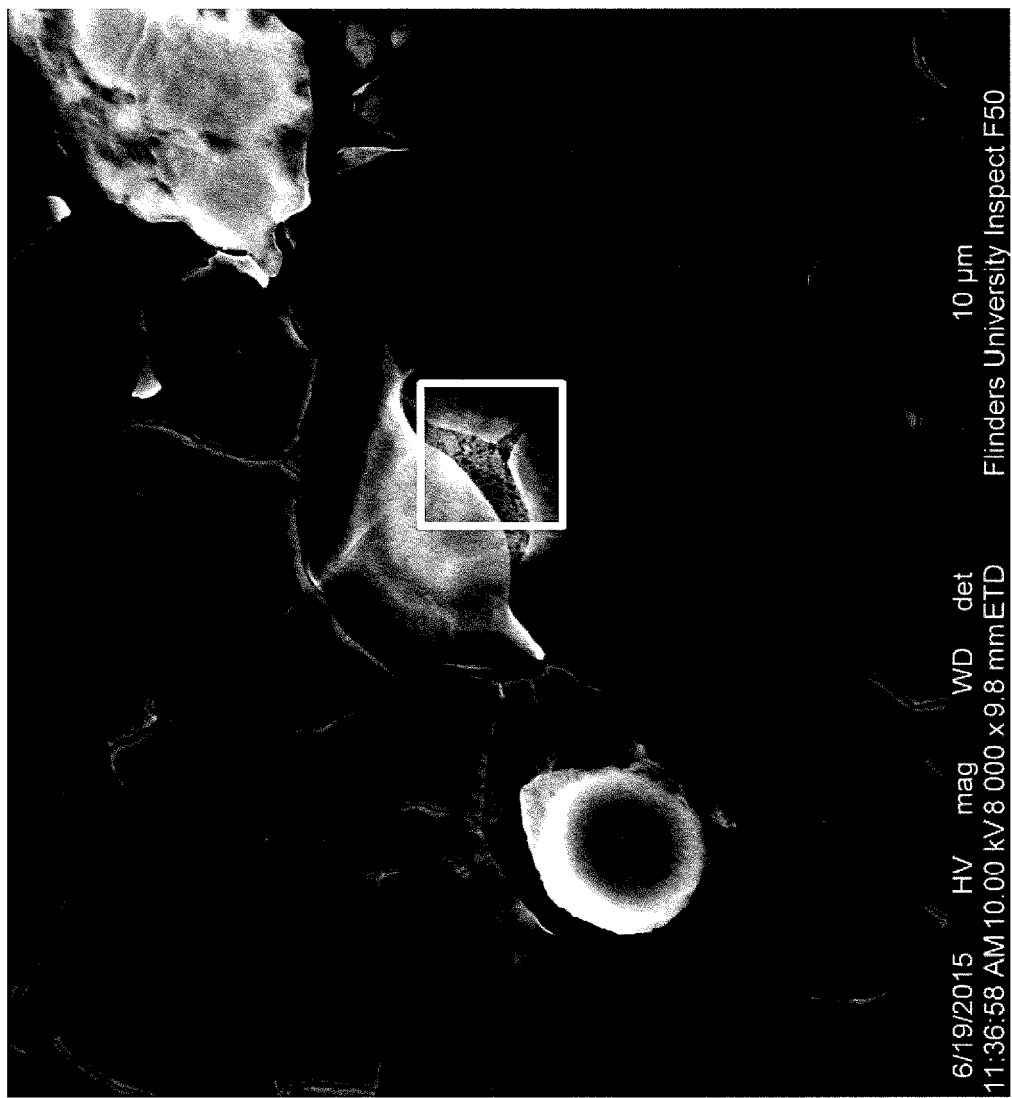
FIG. 30 is an enlargement of the area identified as EDS Spot 5 with the identified region in the box in FIG. 27.
Figure 31:
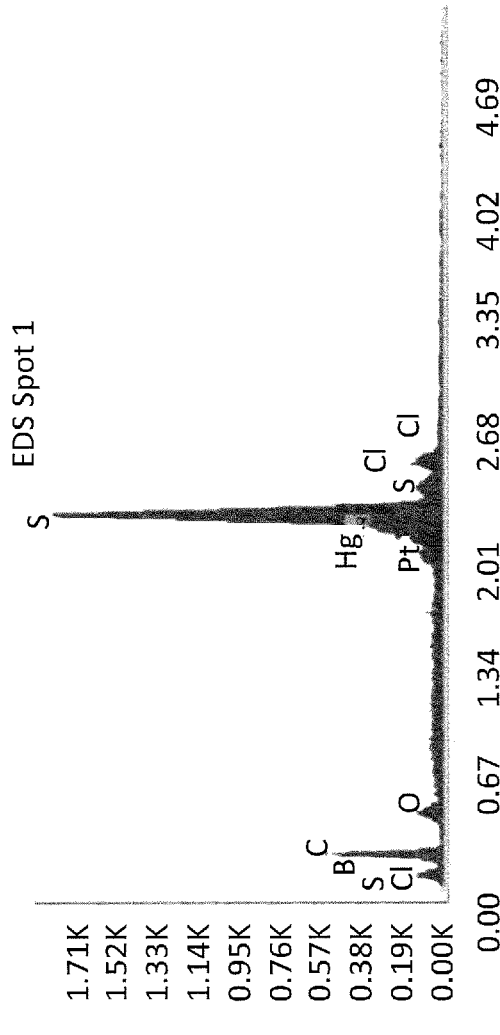
FIGS. 31-35 are the scans produced by the energy dispersive x-ray analysis for each spot identified in FIG. 27.
Figure 32:
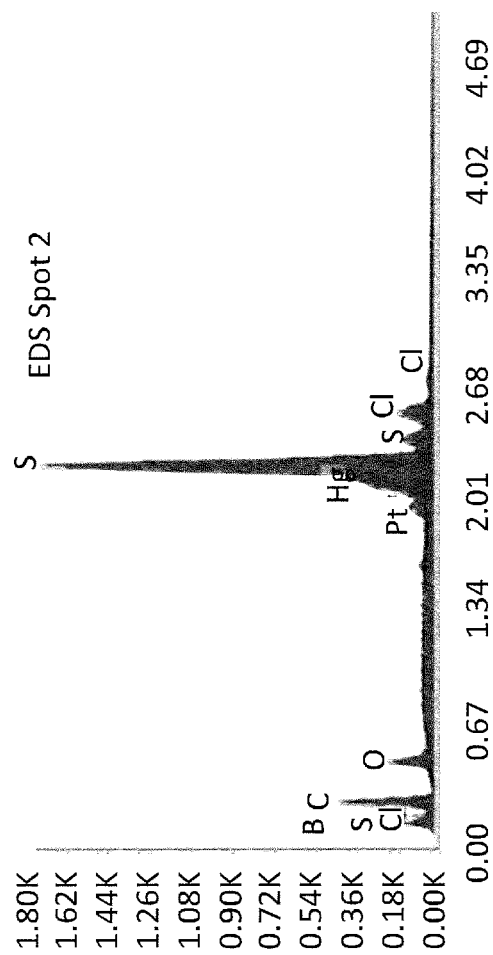
Figure 33:
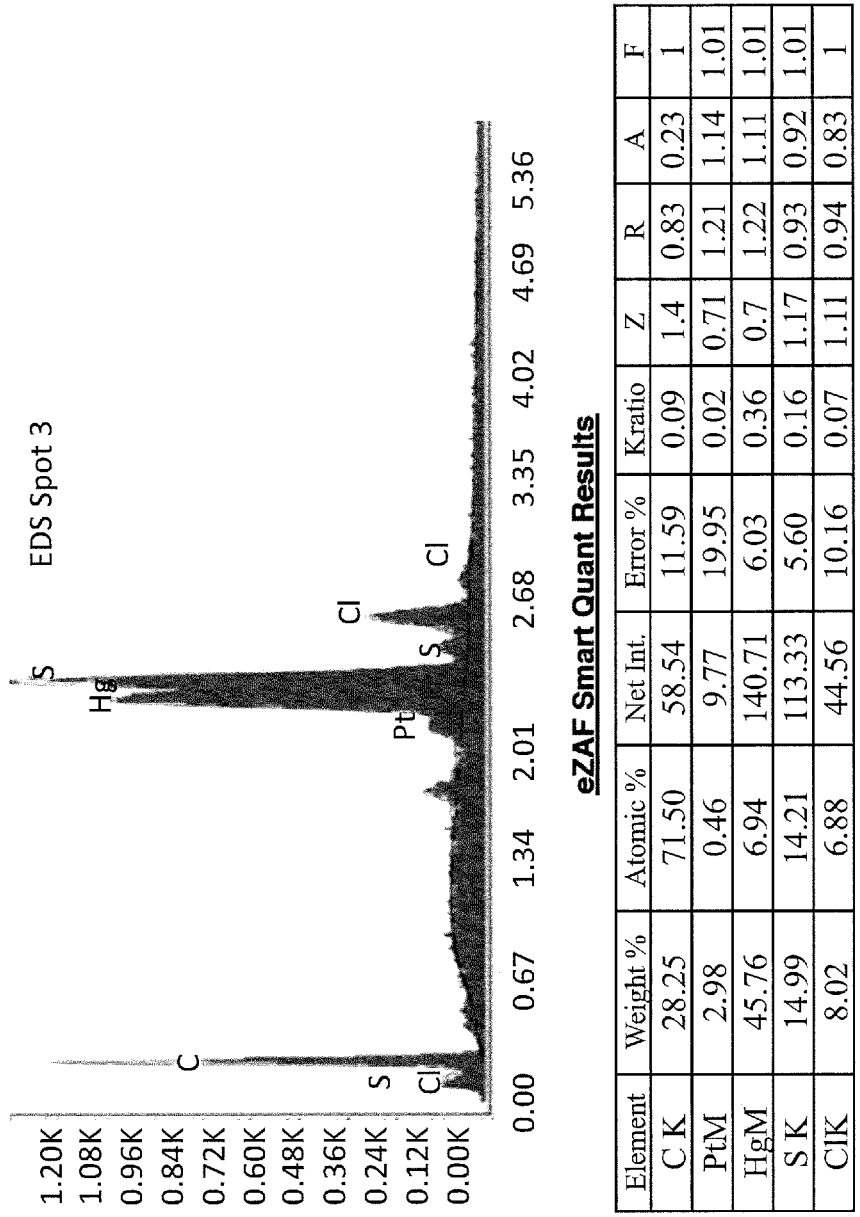
Figure 34:
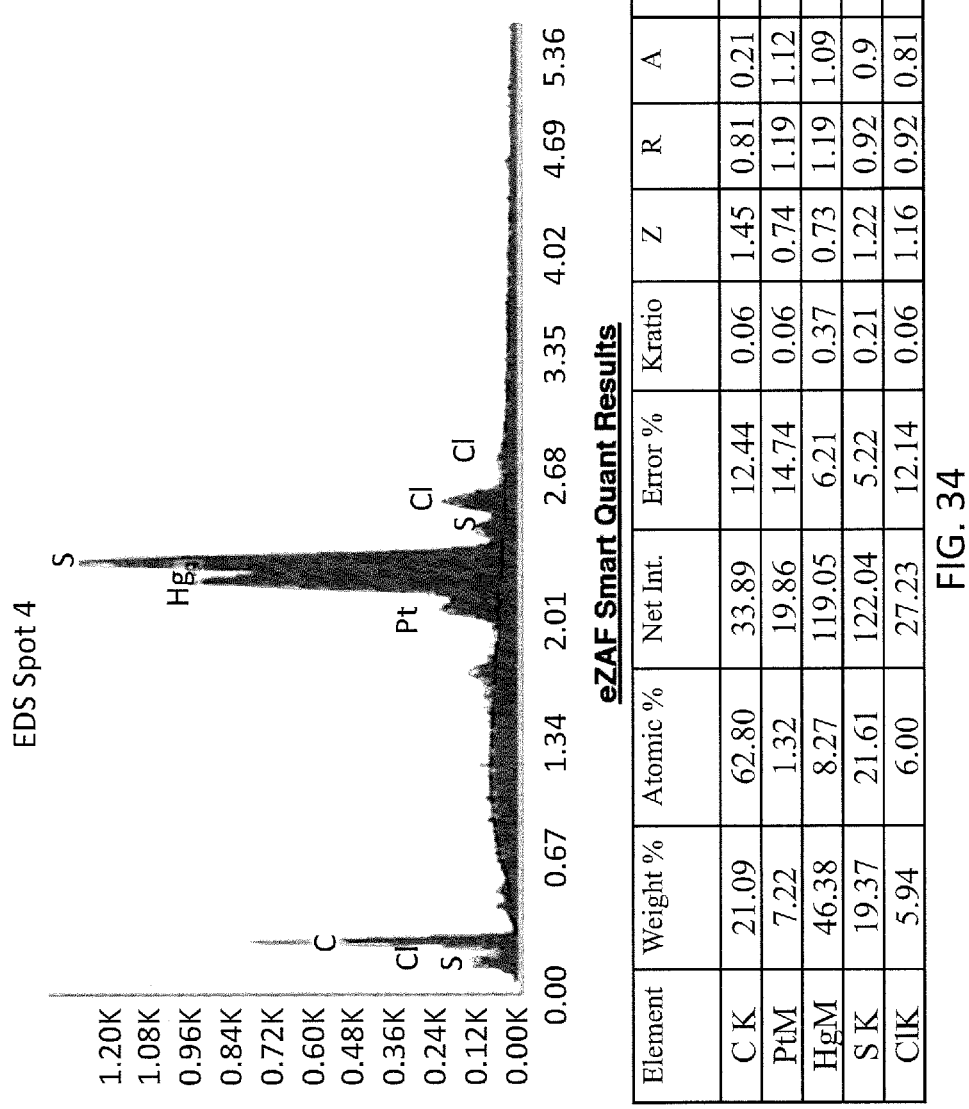

FIGS. 27-30 provide further SEM images of mercuric sulfide particles on the surface of the polysulfide. FIG. 28 is an enlarged view of EDS spot 3 in FIG. 27. FIG. 29 is an enlarged view of EDS spot 4 in FIG. 27 and FIG. 30 is an enlarged view of EDS spot 5 in FIG. 27, FIGS. 31-35 depict the results of the EDS analysis of the spots in FIG. 27.

Figure 35:
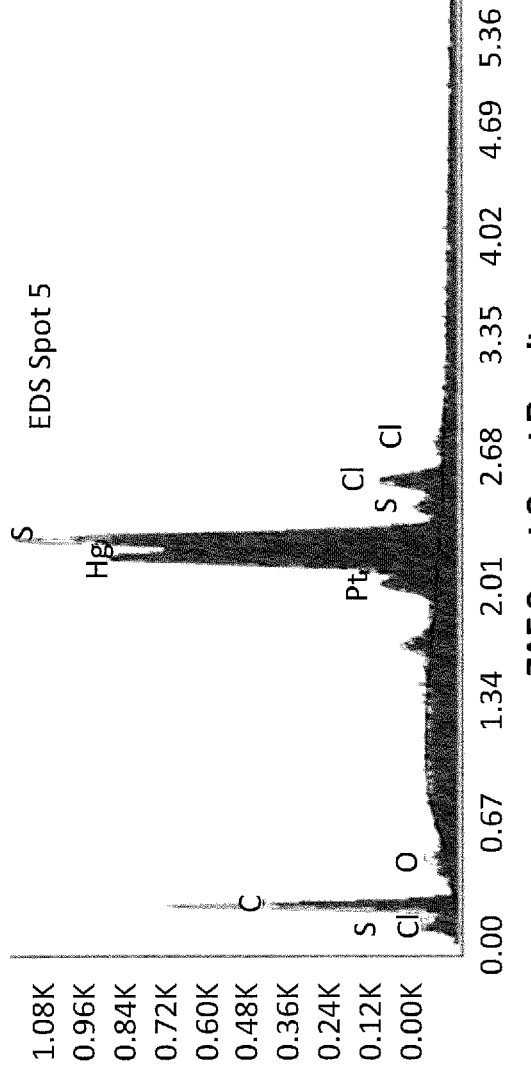

In FIG. 27, EDS spot 1 corresponds to a region lacking micro- and nano-particles but exposed to $HgCl_2$. As a result, mercury appears in the resulting analysis at a concentration of 7.5 weight percent. EDS spot 2 corresponds to a region having an altered surface following exposure to the $HgCl_2$ solution. In the region of EDS spot 2, the surface has become rippled. The EDS analysis depicted in FIG. 32 reflects the binding of mercury to the surface at ten percent by weight. Thus, the rippling may evidence the beginning of the formation of a chemical bind, i.e. the precursor to a particle. EDS spot 3 corresponds directly to a particle as identified in FIG. 27. The EDS scan of FIG. 33 clearly reflects the formation of a mercuric sulfide compound as the scan evidences the presence of 45.8 weight percent mercury at this location. Similarly, EDS spot 4 corresponds to a mercuric sulfide particle that has been partially enveloped by the polysulfide. The presence of mercuric sulfide in the area of EDS spot 4 is confirmed by the EDS analysis of FIG. 34 which reflects the presence of 46 weight percent mercury at the indicated location. Additionally, the EDS analysis indicates the atomic ratio of S to Hg is 21.6 to 8.3. Finally, FIG. 35 provides the EDS analysis of EDS spot 5. EDS spot 5 corresponds to the same particle as EDS spot 4; however, the x-ray analysis was conducted through the opening in the surface of the polysulfide. The resulting EDS scan provides atomic ratios of Hg to S that generally correspond to the scan of FIG. 34.

The resulting polysulfide has a high affinity for sequestering palladium and mercury salts. Over the years, the extensive use of palladium and palladium salts as catalysts in organic synthesis has resulted in palladium contamination of soil and water ways. Likewise, industrial usage of mercury compounds has also produced environmental contamination. The unique characteristics of the above described polysulfide offer an effective route for removing palladium and mercury from the environment.

In the method of the current invention, a polysulfide formed into an object using the methods described above is exposed to water or a soil/water suspension contaminated with $Pd^{2+}$ and/or $Hg^{2+}$. At temperatures between about 4° C. and 60° C., more typically 4° C. to 30° C., a sample of polysulfide having an area of 28 $cm^2$ will reduce the concentration of $Pd^{2+}$ (also known as palladium (II)) by approximately 40 to 60 percent over a two hour period. Under the same operating conditions, the polysulfide will reduce the concentration of $Hg^{2+}$ (also known as mercury (II)) by about 40 to about 60 percent over a two hour period. The method may be practiced by applying the contaminated water to the surface of the polysulfide or by immersing the polysulfide in a body of water, e.g. a pond, stream or lake, and allowing the reaction to progress. During the reaction process, regular sampling of the contaminated water and use of conventional UV-Vis analysis will allow one to determine the progress of palladium remediation. To monitor the progress of mercury remediation, one can simply monitor the polysulfide for the color change from red to yellow. Additionally, $Hg^{2+}$ concentration in water can be determined and monitored using cold vapor atomic absorption spectroscopy.

Remediation of soil may be carried out by initially generating a soil in water suspension. Typically, the soil in water suspension will have from about 400 to 800 grams of soil per liter of water. The suspension will be maintained by stirring for about one to thirty minutes at a temperature of about 4° C. to 60° C., more typically 4° C. to 40° C. Following establishment of the suspension, the polysulfide may be immersed or otherwise contacted with the soil/water suspension for a period of time sufficient to allow for the reaction of $Pd^{2+}$ and/or $Hg^{2+}$ to occur at the surface of the polysulfide. Alternatively, an extraction step may be carried out to isolate the $Pd^{2+}$ and/or $Hg^{2+}$ in a solution free of soil. One suitable extraction process is known as the Soxhlet process. Following extraction of the metals from soil, the method continues as described when remediating contaminated water samples.

The following examples demonstrate the ability of the polysulfide to sequester inorganic palladium. In particular, the examples demonstrate that use of a polysulfide having 28 $cm^2$ surface area in the above described method will result in the reduction of $Pd^{2+}$ concentration by 40% to 60% over a two hour period of exposure. Increasing the surface area of the polysulfide will decrease the time period required for remediation and result in higher removal rates. Additionally, the following examples demonstrate that a polysulfide having 28 $cm^2$ surface area has the ability to reduce $Hg^{2+}$ by at least 55% over a three hour period when treated at 15° C. to 20° C.

For each example, the polysulfide was prepared as described above with removal of volatile materials by vacuum distillation. The polysulfide was then heated to >100° C., poured into a glass petri dish (6 cm diameter) and allowed to cool to room temperature, thereby forming a polysulfide object. The 3 mm thick polysulfide object had an optically transparent, red coloration such that an image can be viewed through the plate. The polysulfide object had a surface area of 28 $cm^2$.

An aqueous solution of $Na_2PdCl_4$ was prepared by adding palladium chloride (3.1 mg, 0.017 mmol) to a 50 mL volumetric flask along with sodium chloride (5.2 mg, 0.088 mmol) followed by 5 mL deionized water. The resulting mixture was dissolved by incubation in an ultrasonication bath for 10 minutes at room temperature. The resulting solution was then diluted to 50 mL with deionized water to provide a 0.35 mM aqueous solution of $Na_2PdCl_4$.

Figure 8:
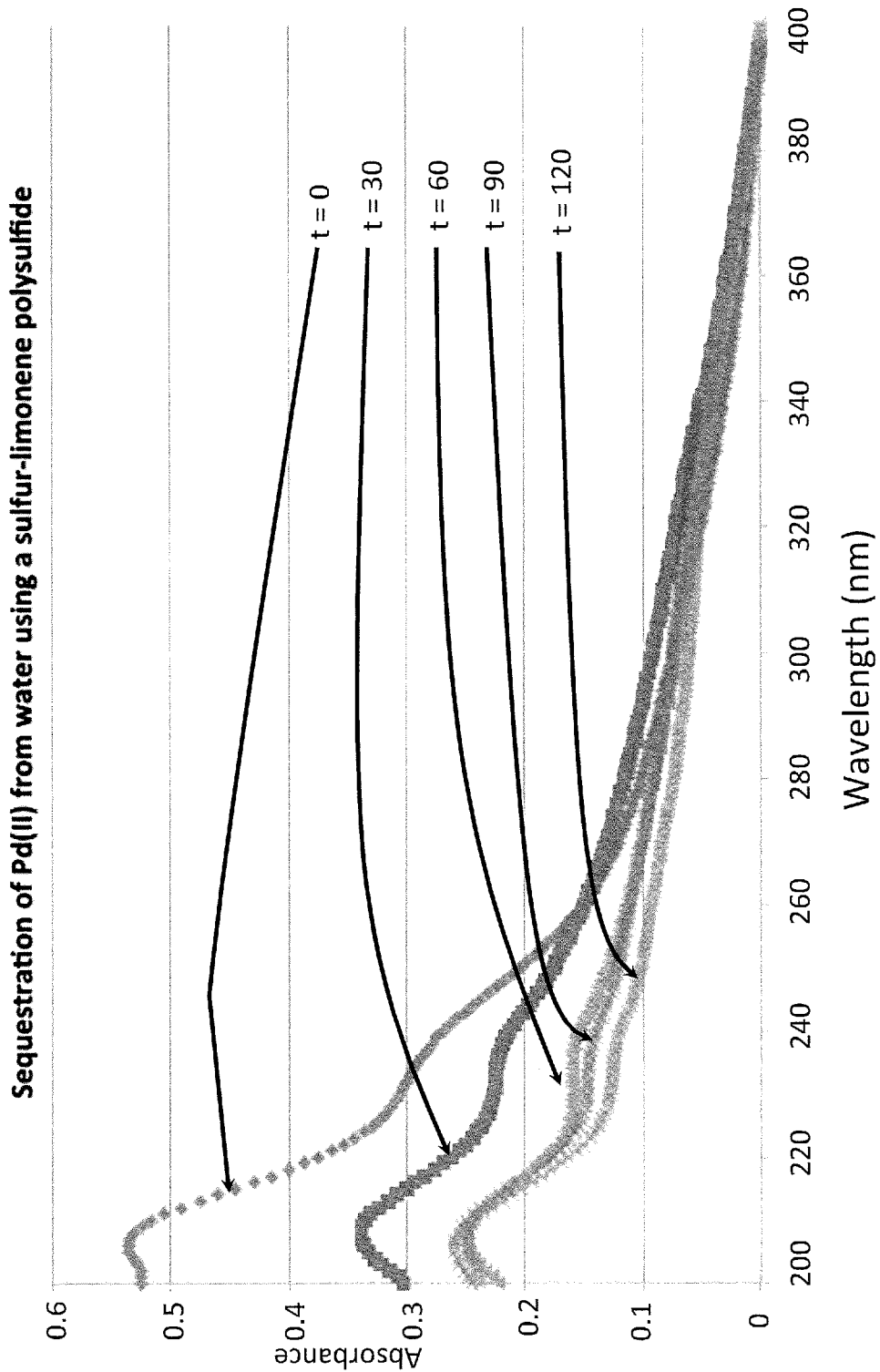
FIG. 8 depicts the UV-Spectrum of $Na_2PdCl_4$ solution after incubation with the polysulfide.

A 10 mL aliquot of the $Na_2PdCl_4$ solution was added to polysulfide products (prepared as described above). The solution was incubated at room temperature on the plates and the UV-Vis spectrum was measured every 30 minutes for 2 hours. In this measurement, an aliquot of the $Na_2PdCl_4$ solution was transferred to a quartz cuvette and the UV-Vis spectrum was obtained before returning the solution to the plate. A clean cuvette was used for each measurement. The UV-Vis spectrum of FIG. 8 depicts the removal of $Pd^{2+}$ from water. Each line in FIG. 8 reflects the UV-Vis spectrum after exposure of the polysulfide to $Na_2PdCl_4$ solution for the indicated time period. As reflected by the change in absorption over time, the spectrum depicts approximately 42% reduction of $Pd^{2+}$ after a period of two hours. Thus, the treatment method lowered the concentration of $Pd^{2+}$ from 0.35 mM to 0.15 mM after two hours. The treatment process can be repeated until palladium levels are lower than regulatory requirements.

Based on the above example, a polysulfide having a surface area of 28 $cm^2$ area can bind between 0.2 and 0.5 mg of $Pd^{2+}$. In view of the thermoplastic characteristics of the polysulfide, a polysulfide coated matrix or polysulfide coated support will permit treatment of contaminated areas such as ponds and streams or even larger bodies of water by immersing the supported polysulfide in the contaminated water. Supporting materials may include, but are not limited to, the interior of a flask or reactor, a stirring device, a polymeric or stainless steel mesh, or other high surface area supporting material that does not react with the polysulfide. Since the reaction occurs at the surface of the polysulfide, the polysulfide layer need be only as thick as that required to bind to the support. The examples discussed herein demonstrate that 28 cm² of limonene-polysulfide surface will remove up to 0.5 mg of $Pd^{2+}$ after an hour of incubation. Subsequently, the supported polysulfide material is removed from the water (or vice versa) leaving purified water and $Pd^{2+}$ bound to the limonene-polysulfide material. As described above, one can easily monitor the remediation process and determine when the polysulfide has become saturated with $Pd^{2+}$ by monitoring water samples with conventional analysis techniques such as UV-Vis analysis. If the polysulfide has become saturated with $Pd^{2+}$ the UV-Vis spectrum will reflect a plateau in the sequestration curve. Likewise, as reflected in FIG. 8, removal of $Pd^{2+}$ to a safe level will be reflected by the UV-Vis spectrum.

To demonstrate the ability to remove inorganic mercury from water, a stock solution of $HgCl_2$ was prepared by dissolving 36.0 mg $HgCl_2$ (133 mmol) in a total volume of 600 μL deionized water. A 0.3 μL aliquot of the stock solution was then diluted to 10.0 mL total volume in water to provide an aqueous solution that is 2 ppm $HgCl_2$. All 10 mL of this solution was then added to the petri dish containing polysulfide prepared as described in the palladium example. The solution was covered and incubated for 24 hours at room temperature. After this time, the solution was removed from the plate and analyzed by cold vapor atomic absorption spectroscopy. The concentration of mercury(II) was measured to be 910 ppb. This experiment shows that a single incubation on the polysulfide plate results in removal of 55% of the mercury.

Additionally, the polysulfide described herein provides the ability to determine the presence of toxic levels of mercury in water. As noted above, the polysulfide has an initial red colorization. However, following exposure to a sufficient quantity of mercury for a sufficient period of time, the polysulfide will undergo a color shift to yellow. The color change typically occurs when 4 cm² of the polysulfide has been exposed to at least 5 mg of mercury(II) in solution, i.e. the concentration of mercury(II) in solution is at least 1 mM. Although some areas of the polysulfide may still be available for further binding of mercury(I) the color change can be used as a signal to indicate the need to replace the polysulfide thereby ensuring that binding of mercury(II) proceeds without delay. However, the lack of color change does not mean that binding of mercury(II) has not occurred. For example, incubation of a solution containing only 2000 ppb $HgCl_2$ on 28 cm² plate of the polysulfide resulted in a reduction of Hg(II) to only 910 ppb, as determined by cold vapor atomic absorption, without changing the polysulfide to yellow. Thus, the color change is associated with remediation of solutions having relatively higher concentrations of mercury(II) or due to long term exposure to lower concentrations of Hg(II). Finally, the color change from red to yellow is unique to this polysulfide. While elemental sulfur is known to bind mercury(II), no color change occurs as a result.

A 2 μL aliquot of the $HgCl_2$ stock solution prepared above (60 mg/mL $HgCl_2$) was diluted to a total volume of 60 μL with deionized water (sample A) and 60 μL of Arkansas River water (sample B). 30 μL aliquots of these solutions (2 mg/mL $HgCl_2$) were then added at different locations on the surface of the polysulfide. The sample plate was incubated for 24 hours at room temperature. After approximately 4 hours, a yellow deposit began to form in the samples containing mercury. Control drops of deionized water (30 μL) did not produce any change in color. After the 24 hour incubation period, the drops were removed by micropipette and the polysulfide surface was washed with deionized water (3×10 mL). Washing did not remove the yellow deposits. This experiment demonstrates the ability to visualize the binding of mercury to the polysulfide at certain concentrations and the adherence of the inorganic mercury to the polysulfide product. Thus, the color change characteristic reflects both the presence of mercury in the water supply and the need to replace the supported polysulfide.

The method for removing inorganic palladium and inorganic mercury may take place in the contaminated environment. Preferably, the method for removing these materials will take place at temperatures between about 4° C. and 30° C. For example, one test exposed a polysulfide prepared as outlined above and having a surface area of 4 cm² to a solution containing 2 mg/mL of mercury (II). The polysulfide effectively sequestered 5 mg of mercury (II) over a period of 180 minutes at a temperature of 15-20° C. Another test exposed a polysulfide prepared as outlined above and having a surface area of 28 cm² to a solution containing 2 μg/mL of mercury (II). The polysulfide effectively sequestered 55% of the mercury (II) present in the solution over a period of 180 minutes at a temperature of 15-20° C. Another test exposed a polysulfide having a surface area of 28 cm² to a solution containing 0.4 mM, i.e. 42% solution, of palladium(II). The polysulfide effectively sequestered 55% of the palladium(II) present in the solution over a period of 120 minutes at a temperature of 15-20° C.

The actual binding reactions occurring during the sequestering process have not been determined. Upon examination of the polysulfide post incubation, the surface of the polysulfide has domains of nano- and micro-particles. Without intending to be bound by theory, we believe that the sequestering step forms nano- and micro-particle domains of mercury sulfides having up to 50 weight percent mercury.

The polysulfide described herein is also useful for remediating mercury(II) contaminated soil. The method of remediating soil includes the following steps: (a) preparing a suspension of contaminated soil in water; (b) maintaining the suspension of soil in water for a period of time sufficient to leach substantially all of the mercury(II) out of the soil; (c) placing the polysulfide in the suspension or passing the water containing mercury(II) from the suspension over the polysulfide. In general, the suspension of soil in water may contain from about 400 to 800 grams of soil per liter of water. The suspension will be maintained by agitation or stirring for about 1 to about 30 minutes at a temperature of about 4° C. to about 60° C., more typically 4° C. to 40° C., prior to introducing the polysulfide to the suspension or filtering the solids and isolating the supernatant containing mercury(II). Suitable equipment for carrying out the extraction of metal contamination from soil would include a Soxhlet extractor. In this method, a soil sample would be placed in the Soxhlet thimble and extracted with hot water for between 30 minutes and 5 hours. The isolated water, now containing mercury(II), would be sent for polysulfide treatment and the purified soil could be returned to the environment. Prior to treating the suspension or supernatant, the concentration of mercury(II) will be determined and used to determine the square centimeters of polysulfide necessary to sequester a sufficient amount of mercury(II) to meet health regulations for water.

To demonstrate the removal of mercury from soil, soil from the bank of Flinders University Lake (~100 g) was suspended in 250 mL of water from the same lake. Before the soil settled, an aliquot of the soil suspension was spiked with $HgCl_2$ so that the final concentration was 100 mM mercury(II). Two samples were then applied in 100 µL aliquots to discrete locations on the surface of a single polysulfide product contained in a petri dish having a surface area of 28 $cm^2$. One sample was a 100 µL aliquot of the mercury-free suspension of pond silt and the other sample was a 100 µL aliquot of the pond silt suspension that had been spiked with 100 mM $HgCl_2$. The petri dish was covered and incubated for 24 hours at room temperature. After 24 hours, both drops appeared brown due to the pond soil. However, after washing the plate with deionized water (3×10 mL), the soil was removed and no soil residue remained on the mercury-free sample. However, a yellow deposit remained on the region treated with the mercury(II)-treated sample. Analysis of the yellow deposits using energy dispersive x-ray (EDX) analysis determined that the deposits contained up to 50 wt % mercury. Thus, the polysulfide can sequester mercury from a complex milieu of pond soil and water. Furthermore, the polysulfide retains the sequestered mercury even after the step of washing. Thus, the foregoing example demonstrates the ability of the polysulfide to remove and retain inorganic mercury from "crude," i.e. unprocessed, soil samples obtained directly from the contaminated environment by merely generating a soil/water suspension and immersion of the polysulfide in the soil/water suspension.

Other embodiments of the present invention will be apparent to one skilled in the art. As such, the foregoing description merely enables and describes the general uses and methods of the present invention. Accordingly, the following claims define the true scope of the present invention.

What is claimed is:

1. A sulfur-limonene polysulfide having an initial red colorization which when exposed to a sufficient concentration of inorganic mercury dissolved in water changes to yellow colorization at the location of inorganic mercury exposure.

2. A sulfur-limonene polysulfide comprising a reaction product of limonene and elemental sulfur wherein said sulfur-limonene polysulfide has a molecular weight between about 386 and about 777 Daltons and said sulfur-limonene polysulfide having an initial red colorization which when exposed to a sufficient concentration of inorganic mercury dissolved in water changes to yellow colorization at the location of inorganic mercury exposure.

3. The sulfur-limonene polysulfide of claim 2, wherein said sulfur atoms may range from 2 to 19 sulfur atoms and said sulfur-limonene polysulfide contains from one to three limonene units.

4. The sulfur-limonene polysulfide of claim 2, wherein said sulfur-limonene polysulfide has a glass transition state of −21° C. as determined by differential scanning calorimetry.

5. The sulfur-limonene polysulfide of claim 2, wherein said sulfur-limonene polysulfide has less than 4% by weight free sulfur.

6. The sulfur-limonene polysulfide of claim 2, wherein said sulfur-limonene polysulfide depolymerizes when heated to a temperature between about 200° C. and 300° C.

7. The polysulfide of claim 2, wherein said polysulfide has an elemental composition of C=38.97%, H=4.97% and S=56.60 percent when measured by combustion analysis using thermal conductivity detection for carbon and hydrogen and ion chromatography for sulfur.

8. A method comprising:
heating sulfur to a temperature sufficient to provide molten sulfur;
adding limonene to said molten sulfur;
heating the mixture of limonene and molten sulfur for a period of time sufficient to yield a single phase, wherein said single phase comprises sulfur-limonene polysulfide, said sulfur-limonene polysulfide having an initial red colorization which when exposed to a sufficient concentration of inorganic mercury dissolved in water changes to yellow colorization at the location of inorganic mercury exposure.

9. The method of claim 8, wherein said step of heating the mixture of limonene and molten sulfur heats the mixture to a temperature between about 130° C. and about 200° C.

10. The method of claim 8, wherein said step of heating the mixture of limonene and molten sulfur heats the mixture to a temperature between about 160° C. and about 175° C.

11. The method of claim 8, wherein said step of heating the mixture of limonene and molten sulfur heats the mixture to a temperature between about 176° C. and about 180° C. and at a pressure between about 6.0 kPa and about 6.7 kPa.

12. The method of claim 8 further comprising the step of removing volatile by-products by heating said single phase to a temperature between about 25° C. to 100° C.

13. The method of claim 8 further comprising the step removing volatile by-products from said single phase by heating said single phase to a temperature between about 100° C. to about 180° C. under a vacuum.

14. The method of claim 8, wherein said sulfur is heated to a temperature between about 120° and 124° C. at atmospheric pressure.

15. The method of claim 8, wherein the ratio of limonene to sulfur may range from about 1:1.5 to about 1.5:1.

16. The method of claim 8, wherein the ratio of limonene to sulfur provides a single phase comprising at least 70% polysulfide by weight.

17. The method of claim 8 further comprising:
removing volatile by-products from said single phase, thereby isolating said sulfur-limonene polysulfide; and forming said sulfur-limonene polysulfide into an object.

18. The method of claim 8 further comprising:
spin coating said single phase comprising said sulfur-limonen polysulfide onto a surface thereby forming a sulfur-limonene polysulfide object and removing volatile by-products in a single step.

19. The method of claim 8 further comprising:
forming said sulfur-limonene polysulfide into a object;
sequestering palladium (II) from an aqueous solution by exposing said sulfur-limonene polysulfide object to an aqueous solution containing palladium (II) wherein said sulfur-limonene polysulfide removes palladium (II) from said aqueous solution.

20. The method of claim 19, wherein said step of sequestering palladium (II) from an aqueous solution by exposing said sulfur-limonene polysulfide object to palladium in an aqueous solution occurs at a temperature between about 4° C. and about 30° C.

21. The method of claim 20, wherein said step of sequestering palladium (II) from an aqueous solution by exposing said sulfur-limonene polysulfide object to palladium in an aqueous solution continues for at least two hours thereby reducing the concentration of palladium (II) in said aqueous solution by at least 40 percent.

22. The method of claim 8 further comprising:
forming said sulfur-limonene polysulfide into a object;
sequestering mercury (II) from an aqueous solution by exposing said sulfur-limonene polysulfide object to an aqueous solution containing mercury (II) wherein said sulfur-limonene polysulfide removes mercury (II) from said aqueous solution.

23. The method of claim 22, wherein said step of sequestering mercury (II) from an aqueous solution by exposing said sulfur-limonene polysulfide object to mercury (II) in an aqueous solution continues for at least two hours thereby reducing the concentration of mercury (II) in said aqueous solution by at least 40 percent.

24. The method of claim 22, further comprising the step of monitoring said sulfur-limonene polysulfide object for a color change from a red to a yellow.

25. The method of claim 8 further comprising:
forming said sulfur-limonene polysulfide into an object;
suspending soil containing palladium (II) in water for a period of time sufficient to extract palladium (II) from the soil thereby providing a water solution containing palladium (II);
isolating the water containing palladium (II) from the soil;
sequestering palladium (II) from said water solution containing palladium (II) by contacting said water solution containing palladium (II) with said sulfur-limonene polysulfide object for a period of time sufficient to permit reaction of said palladium (II) with said sulfur-limonene polysulfide.

26. The method of claim 25, further comprising the step of monitoring the reaction of said palladium (II) with said sulfur-limonene polysulfide by measuring the UV-Vis transmittance of said water containing said palladium (II).

27. The method of claim 8 further comprising:
forming said sulfur-limonene polysulfide into an object;
suspending soil containing mercury (II) in water for a period of time sufficient to extract mercury (II) from the soil thereby providing a water solution containing mercury (II);
isolating the water containing mercury (II) from the soil;
sequestering mercury (II) from said water solution containing mercury (II) by contacting said water solution containing mercury (II) with said sulfur-limonene polysulfide object for a period of time sufficient to permit reaction of said mercury (II) with said sulfur-limonene polysulfide.

28. The method of claim 27, further comprising the step of monitoring the reaction of said mercury (II) with said sulfur-limonene polysulfide by monitoring said sulfur-limonene polysulfide for regions which change in color from red to yellow.

29. A sulfur-limonene polysulfide, said sulfur-limonene polysulfide having an initial red colorization which when exposed to a sufficient concentration of inorganic mercury dissolved in water changes to yellow colorization at the location of inorganic mercury exposure and which when formed into a sulfur-limonene polysulfide object having a surface area of 4 cm$^2$ will bind at least about 5 mg of mercury (II) over a period of 180 minutes at a temperature of about 15° C. to about 20° C.

30. The sulfur-limonene polysulfide of claim 1, wherein said sulfur-limonene polysulfide has a molecular weight between about 386 and about 777 Daltons.

31. The sulfur-limonene polysulfide of claim 1, wherein said sulfur-limonene polysulfide has a glass transition state of −21° C. as determined by differential scanning calorimetry.

32. The sulfur-limonene polysulfide of claim 1, wherein said sulfur-limonene polysulfide has less than 4% by weight free sulfur.

33. The sulfur-limonene polysulfide of claim 1, wherein said sulfur-limonene polysulfide depolymerizes when heated to a temperature between about 200° C. and 300° C.

34. The polysulfide of claim 1, wherein said polysulfide has an elemental composition of C=38.97%, H=4.97% and S=56.60 percent when measured by combustion analysis using thermal conductivity detection for carbon and hydrogen and ion chromatography for sulfur.

35. A sulfur-limonene polysulfide, said sulfur-limonene polysulfide having an initial red colorization which when exposed to a sufficient concentration of inorganic mercury dissolved in water changes to yellow colorization at the location of inorganic mercury exposure and which when formed into a sulfur-limonene polysulfide object having a surface area of 28 cm$^2$ will reduce the concentration of 0.35 mM aqueous solution of palladium (II) by at least 40% when said sulfur-limonene polysulfide object is contacted with said solution over a two hour period.

* * * * *